(12) United States Patent
Graham et al.

(10) Patent No.: US 7,705,202 B2
(45) Date of Patent: Apr. 27, 2010

(54) TRANSGENIC PLANTS EXPRESSING ENZYMES INVOLVED IN FATTY ACID BIOSYNTHESIS

(75) Inventors: Ian Alexander Graham, York (GB); Thierry Tonon, Roscoff (GB)

(73) Assignee: The University of York, York (GB)

( * ) Notice: Subject to any disclaimer, the term of this patent is extended or adjusted under 35 U.S.C. 154(b) by 1325 days.

(21) Appl. No.: 10/508,109

(22) PCT Filed: Mar. 17, 2003

(86) PCT No.: PCT/GB03/01099

§ 371 (c)(1),
(2), (4) Date: Mar. 22, 2005

(87) PCT Pub. No.: WO03/078639

PCT Pub. Date: Sep. 25, 2003

(65) Prior Publication Data

US 2005/0164192 A1    Jul. 28, 2005

(30) Foreign Application Priority Data

| Mar. 16, 2002 | (GB) | ................................. | 0206308.9 |
| May 25, 2002 | (GB) | ................................. | 0212133.3 |
| Jul. 11, 2002 | (GB) | ................................. | 0216013.3 |
| Nov. 1, 2002 | (GB) | ................................. | 0225489.4 |

(51) Int. Cl.
*A01H 5/00* (2006.01)
*C12N 15/82* (2006.01)
*C07H 21/04* (2006.01)

(52) U.S. Cl. .................... 800/298; 800/281; 435/320.1; 435/410; 536/23.2

(58) Field of Classification Search ....................... None
See application file for complete search history.

(56) References Cited

FOREIGN PATENT DOCUMENTS

| WO | WO 00/55330 A | 9/2000 |
| WO | WO 01/59128 A | 8/2001 |

OTHER PUBLICATIONS

Qiu et al, JBC 276 (34): 31561-31566, Aug. 2001.*

* cited by examiner

*Primary Examiner*—Elizabeth F McElwain
(74) *Attorney, Agent, or Firm*—Janet Sleath; Speckman Law Group PLLC

(57) ABSTRACT

This invention relates to nucleic acid molecules which comprise nucleic acid sequences which encode enzymes involved in the biosynthesis of n-3 fatty acids, particularly docosahexanoic acid (DHA), or variants thereof; polypeptides encoded by said nucleic acids; cells transfected with said nucleic acid sequences and products comprising said nucleic acid sequences, polypeptides and/or cells.

20 Claims, 13 Drawing Sheets

Figure 1a

```
CACGAGGCCTCGTGCCGAATTCGGCACGAGGGCTGCGCGACGACAAGGAC
GACGGCAGCCTGAGTGCGACGAGCGATTTCTTCCGCTCGACGATCACGGA
TTGCGGCAATTTTTGCGACGAGTCGGTCGACTTCCAGATGAAGCTTTTTG
AGCGCAACCAGATCTCCGAGCGCTGCTACTTCCCACCTGGCATCCGCGCC
TACCGCAAGGGCGAGCGCGACTTTGACTTTTCGATGGCCGCCGCGCGCAA
GGAGTTCGAGACTGTCGTCTTCACGACCGTCGACGAGCTGCTCGCCAAGA
CGGGCGTAAAGCCGCGAGATATCGACATCCTCGTCGTCAACTGCTCGCTC
TTCAACCCGACGCCATCGCTGGCTGCGATCGTGATCAACCACTACCAGAT
GAAGGACTCCGTACAGAGCTACTCACTTGGCGGGATGGGTTGCTCAGCGG
GACTCATCTCAATCCACCTCGCAAAGGACCTGCTGCAGGTCTACCCGCGC
AAGCGCGCGCTCGTCATCTCGACGGAGAACATCACGCAAAATTTTTACCA
GGGCAACGAAAAGTCGATGCTCATCTCGAACACGCTCTTCCGAATGGGCG
GCGCCGCCGTCCTCCTCTCCGGCCGCCACGCCGACCGGCGCGTCGCCAAG
TATCAACTGCTGCACACCGTCCGCACGCACAAGGGCGCGGACCCGGACGC
GTACCGGTGCGTCTTCCAGGAGGAGGACAAGGCGGGGCACGTGGGCGTGC
GCCTGTCGAAAGACGTGATGGAGTGCGCCGGCGCCGCGATGAAGACCAAC
ATCTCCGTCCTCGCGCCTCTGATTCTGCCCGTTTCTGAGCAGGTCCGATT
TCTCGCAAACTACGTTGCGCGCAAGTGGCTGCGAATGAAAGGCGTGAAGG
GATACGTGCCGGACTTCACAACGGCCGTGCAGCACTTTTGCATCCACACG
GGCGGGCGCGCGGTGCTCGACGCGCTGCAGGCGAACTTGTCGCTCTCAGA
TTACTACCTCGAGCCGAGCCGTTACTCCCTGTGGCGCTGGGGTAACGTCT
CAAGCGCCTCAGTCTGGTACGAGCTCGACTGGCTCGAAAAGTCCGGCCGC
ATCCGGCGGGGCGACAAGGTGTGGCAGATTGGGTTTGGCAGCGGCTTCAA
GTGCAACTCGGCCGTCTGGCGGGCGTGCCGAGCGATGCCCTAGCTACGCC
GGCGCCGTCCGCATTGCCAGTGGTTCGTGACAGACAGTCACACTGACGAG
TGCGGAGTGACGTCTGACGCCTTCCCCCCCCCGCCCACCACCTCCACCTC
CACCTCCTTCACTCTCACTCAATCGCGCGGCGGCCAGAGCAGGAGCGCGC
TCGTGCTCGCCATCACCGCCTTGTAGTCCTCGCGCCGCTCGAGCGAGCGC
GCGTCCATGAGCGGCACGGACGCGAAGCGGAAGAAGAGCCACATCACAGC
AGAAAAAAAAAAAAAAAAAAAACTCGAGACTAGTTCTCTCTACCGCGCTGC
CGAGCTCAAGCACGGCCGCGTGTGCATGCTCGCCGTCACCGGCATGCTTG
TCCAGGAGGTGTACTCGTGGCCGGCACCCGACGGCGTCTTCAAGGCGCCG
ACGCCGCTCGGCGCGCTCTCGACCGTGCCGGCGCTCGGCCTCATCCAGCT
CATCGTCTTCCTCGGCATCATCGAGGTGCGCTCGGCGAACTACCAGGGCC
GCGTGCCCGGCGACCTTGGCTTTGACCCGCTCGG
```

```
GCACGAGGCCTCGTGCCGAATTCGGCACGAGGCGGCGCTGTGGTCGTGGT
TACCGACGTACGACGAGTTTGTCGATGGGCTTTCGTTCGTCGACCGCGAG
AAGATCGGCGTGCACATGGTCGACCAGGGCGTGATTACCTCTGCGGAGTG
GGCGGCCATCTCGGTCGACAAGCACATGTCCTTCTTCTCCGACGCGGCCG
AGTTCACGGGCGACCACTGGATCATCCCGCTCGTCGCGGTCGCACTCTAC
CTCGTGATGATCGTCGTCGGCCCAATGATCATGGCCAACCGGCCGCCGCT
CCCCGTGAATGGGCTCGCCTGCGCGTGGAACTGGTTCCTGGCCGCATTCA
GCACTTTCGGCGTGGCTTGCACGTGGCACTGTATCTTCACCAGGCTGCGT
AGCCGCGGCTTCGAGAGCACGACGTGCGGCAGCGCCATGTTCATGTCGCA
GGGGTACGTTGGCTTGGCAATGCTGCTCTTCATCTACTCCAAGCTCTTCG
AGTTGATCGACACCTTCTTCCTCATCGCGAAGAAGGCGGATGTGATCTTC
CTGCATTGGTACCACCACGTCACCGTGCTGCTCTACTGCTGGCACTCGCA
CTCGGTCCGGATACCGAGCGGGATCTGGTTCGCCGCGATGAACTACTTTG
TGCACGCCATCATGTACTCCTACTTTGCGATGACGCAGATGGGTCCGCGC
TACCGCAAGCTCGTCCGGCCGTACGCGCGGCTGATTACGACCCTGCAGAT
CTCGCAGATGTTCGTCGGCCTCATCGTCAACGGCTCGATCATTTACTTCA
CGTCGCTCGGGCACGCATGCAAGTCGAGCAAGACGAACACGATCCTGAGC
TGGCTGATGTACCTCAGCTACTTTGTGCTATTCGGACTGCTCTACCTGCG
CAATTACATCCTTGGTACACATGGCAAGCCGGCGGGCAAGCGCGCAAAGG
GCAAGGCGGAATAGTGCAGGGGCCGGGGAGGCGGTGCCCACCCGCGCTCG
CAAAGCGGTCGCGCTCCTTGCCGAGATGCGACGAGAGTCGAAGAGGTGAA
ACCTCCTTAAAATAATGCTACTCCTAGATTTTCGCTTTGTGCTTCCGTAT
AGATGGTCAAGCC
```

```
CACGAGGCGAATGTGGGCGGCTACTGGCTTGGCGTGCTCAATGGAGGGCT
CAACTTCCAGATCGAGCACCATCTTTTCCCGCGGCTGCACCATTCGTACT
ACGCGCAGATTGCCCCAGTGGTGCGCACGCACATCGAGAAGCTCGGCTTC
AAGTACAGGCACTTCCCCACGGTGGGCTCCAACTTGTCGTCCATGCTGCA
GCACATGGGCAAGATGGGCACTCGCCCAGGAGCTGAGAAGGGCGGCAAGG
CCGAGTGAGCTGCCGCCCTACCCTGCCTCTGCGGCTAGCCAGCAACCGGG
TGCCAGCGAGCCCCTCTTCCATCCGAGCCCTTTTCTCCTTCACCCTGCCA
TGTGTCAGCGGCACTGACTGAACTGACGTCGCCGTGCCGCTGGCGCTCTC
CGTCGCCAGCCACTGAGAGGCTGCAATGCCGCCCGACGCCGCTCACGCGG
CTTTGGTCTTAAAAAAAAAAAAAAAAAAAAA
```

```
MPPSAASEGG VAELRAAEVA SYTRKAVDER PDLTIVGDAV YDAKAFRDEH PVGAHFVSLF
GGRDATEAFM EYHRRTWPKA RMSKFFVGSL DASEKPTQAD SAYLRLCAEV NALLPKGSGG
FAPPSYWLKA AALVVAAVSI EGYMLLRGKT LLLSVFLGLV FAWIGLNIQH DANHGALSRH
SVINYCLGYA QDWIGGNMVL WLQEHVVMHH LHTNDVDADP DQKAHGVLRL KPTDGWMPWH
ALQQLYILPG EAMYAFKLLF LDALELLAWR WEGEKISPLA RALFAPAVAC KLGFWARFVA
LPLWLQPTVH TALCICATVC TGSFYLAFFF FISHNFDGVG SVGPKGSLPR SATFVQRQVE
TSSNVGGYWL GVLNGGLNFQ IEHHLFPRLH HSYYAQIAPV VRTHIEKLGF KYRHFPTVGS
NLSSMLQHMG KMGTRPGAEK GGKAE
```

Figure 3d

ACGCGGTGTCACGCGCGTCTTCCAGCGCGAGCCGCTGCTCCGCCGCGAAGTCTCTAGGCATGCCGCCTTCGGCCGCGAGCGAGGGCGGC
GTGGCGGAGCTGCGCGCGGCGGAGGTCGCCTCGTACACGCGCAAGGCGGTGGATGAGCGCCCCGACCTCACCATCGTCGGCGATGCCGT
CTACGACGCCAAGGCCTTCCGTGACGAGCACCCGGTCGGCGCCCACTTTGTGAGCCTCTTTGGCGGGCGCGACGCGACCGAGGCGTTCA
TGGAGTACCACCGGCGGACGTGGCCCAAGGCGCGGATGAGCAAGTTCTTCGTGGGCTCGCTCGACGCCTCCGAGAAGCCGACGCAGGCC
GACAGTGCCTACCTCCGGCTGTGCGCGGAGGTGAACGCCTTGCTGCCAAAGGGGAGCGGCGGCTTTGCGCCGCCCTCCTATTGGCTCAA
GGCGGCGGCGCTGGTGGTGGCCGCCGTGTCGATTGAGGGGTATATGCTGCTGCGCGGCAAGACGCTCCTCCTCTCCGTCTTTCTCGGCC
TCGTCTTTGCGTGGATCGGTCTCAACATCCAGCACGACGCGAACCACGGCGCGCTCTCGCGCCACTCGGTGATCAACTACTGCCTTGGG
TACGCGCAGGACTGGATCGGCGGCAACATGGTGCTCTGGCTGCAGGAGCACGTGGTGATGCACCACCTGCACACCAACGACGTCGACGC
CGACCCGGACCAGAAGGCGCACGGCGTGCTGCGGCTCAAGCCAACGGACGGCTGGATGCCGTGGCATGCGCTCCAACAGCTTTACATTC
TGCCCGGCGAGGCGATGTACGCGTTTAAGCTGCTCTTCCTCGACGCGCTCGAGCTGCTCGCGTGGCGATGGGAGGGCGAGAAGATCTCG
CCCCTCGCGCGCGCCCTGTTTGCACCAGCGGTGGCGTGCAAGCTTGGCTTCTGGGCGCGCTTCGTCGCGCTGCCGCTCTGGCTGCAGCC
GACGGTGCACACGGCGCTGTGCATCTGCGCGACGGTGTGCACGGGCTCCTTCTACCTCGCCTTCTTCTTCTTCATCTCGCACAACTTTG
ACGGCGTGGGTAGTGTGGGCCCCAAGGGCAGCTTGCCGCGCTCTGCAACCTTCGTGCAGCGGCAGGTCGAGACGAGTTCGAATGTGGGC
GGCTACTGGCTTGGCGTGCTCAATGGAGGGCTCAACTTCCAGATCGAGCACCATCTTTTCCCGCGGCTGCACCATTCGTACTACGCGCA
GATTGCCCCAGTGGTGCGCACGCACATCGAGAAGCTCGGCTTCAAGTACAGGCACTTCCCCACGGTGGGCTCCAACTTGTCGTCCATGC
TGCAGCACATGGGCAAGATGGGCACTCGCCCAGGAGCTGAGAAGGGCGGCAAGGCCGAGTGAGCTGCCGCCCTACCCTGCCTCTGCGGC
TAGCCAGCAACCGGGTGCCAGCGAGCCCCTCTTCCATCCGAGCCCTTTTCTCCTTCACCCTGCCATGTGTCAGCGGCACTGACTGAACT
GACGTCGCCGTGCCGCTGGCGCTCTCCGTCGCCAGCCACTGAGAGGCTGCAATGCCGCCCGACGCCGCTCACGCGGCTTTGGTCTTAAA
AAAAAAAAAAAAAAAAA

Figure 4a

```
GCACGAGGGTGCTGCTACCTGCTGTACGTCTCCCTCGGCTCGATGTACAT
CTTCTGCAACTTTGCCGTGTCGCACACGCACCTGCCCATCGTTGAGGCCG
ACCAGCACGCCACCTGGGTTGAGTACTCGGCCAACCACACGACCAACTGC
GCGCCCTCGTGGTGGTGCGACTGGTGGATGTCTTACCTCAACTACCAGAT
CGAGCATCATCTGTTCCCGTCCATGCCGCAATTCCGCCACCCGACGATCG
CGCCGCGCGTCAAGGCGCTCTTCGAGAAGCACGGGCTGCACTATGACGTG
CGCGGCTACTTTGAGGCGATGGCCGACACGTTCATGAACCTTGACAAGGT
CGGCAACGCGCACGAGCACAACCATTAGGCCGTAGCCGCTTGGAAAGAGG
CCTCCTGCATACGCGGCGACGCGTCGGCGCGCGGCGGCGTGCACGGGAGC
ACAAAGTGATGGATGGACCTTGGGCGACGCCGACGGCCAAGGAGTGGTTG
TCTCTGTCGTCGCCAGGGCCCAGGAGCCCAGGGGCAGGGTTGCAGAGCTT
GGGCGCGATTGGAGGCAGGGCCGGGCGCGTCGGCGTTCGCGAGTCTGGCG
AGGCGCTCTGCGAGCTCTGCACGACTGCGCCCAGAGGCGTGCGCGCGCGC
GCGAGTTCCAAAAAAAAAAAAAAAAAAAAAAAA
```

```
TspFAD4    MTVGYDEEIPFEQVRAHNKPDDAWCAIHGHVYDVTKFASVHPGGDIILLAGKEATVLYET
P1DES1     ------------------------------------------------------------
P1DES2     ------------------------------------------------------------

TspFAD4    YHVRGVSDAVLRKYRIGKLPDGQGGANEKEKRTLSGLSSASYYTWNSDFYRVMRERVVAR
P1DES1     ------------------------------------------------------------
P1DES2     ------------------------------------------------------------

TspFAD4    LKERGKARRGGYELWIKAFLLLVGFWSSLYWMCTLDPSFGAILAAMSLGVFAAFVGTCIQ
P1DES1     ------------------------------------------------------------
P1DES2     ------------------------------------------------------------

TspFAD4    HDGNHGAFAQSRWVNKVAGWTLDMIGASGMTWEFQHVLGHHPYTNLIEEENGLQKVSGKK
P1DES1     ------------------------------------------------------------
P1DES2     ------------------------------------------------------------

TspFAD4    MDTKLADQESDPDVFSTYPMMRLHPWHQKRWYHRFQHIYGPFIFGFMTINKVVTQDVGVV
P1DES1     ------------------------------------------------------------
P1DES2     ------------------------------------------------------------

TspFAD4    LRKRLFQIDAECRYASPMYVARFWIMKALTVLYMVALPCYMQGPWHGLKLFAIAHFTCGE
P1DES1     ------------------------------------------------------------
P1DES2     ------------------------------------------------------------

TspFAD4    VLATMFIVNHIIEGVSYASKDAVKGTMAPPKTMHGVTPMNNTRKEVEAEASKSGAVVKSV
P1DES1     ------------------------------------------------------------
P1DES2     --------------------------------ARGCCYLLYVSLGSMYIFCNFAVSHTHLPIV

TspFAD4    PLDDGWAVVQCQTSVNWSVG-SWFWNHFSGGLNHQIEHHLFPGLSHETYYHIQDVFQSTC
P1DES1     --------------HEANVG-GYWLGVLNGGLNFQIEHHLFPRLHHSYYAQIAPVVRTHI
P1DES2     EADQHATWVEYSANHTTNCAPSWWCDWWMSYLNYQIEHHLFPSMPQFRHPTIAPRVKALF

TspFAD4    AEYGVPYQHEPSIWTAYWKMLEHLRQLGNEETHESWQRAA
P1DES1     EKLGFKYRHFPTVGSNLSSMLQHMGKMGTRPGAEKGGKAE
P1DES2     EKHGLHYDVR-GYFEAMADTFMNLDKVGNAHEHNH-----
```

Figure 6a

```
GCACGAGGCCTCTTCGGCTGGGCGCTCGACGACGCGCTCGCCAAGTATGA
CAAGGGCGGCGTCGGCCCCGGCTTCCTGTACAACGCGGTCGTCTTCTCGT
CGGTGCAGGCGCTGCTCGGCGGTCGCGTGCGCATGATGGTCGCCGGCTCC
GCGCCCCTCTCCGCCGACGTGCAGAAGTTTGTGCAATCGTGCTTCAACGC
GCCGCTTCGCCAAGGCTACGGCCTCACCGAGACGTGCGCGGCGACGACGC
TCTGCGCGCTGCACGACAACACGCCGTCGCAAGTTGGGCCGCCGCAGGAG
TCGGCGTGCATCACGCTGCGCGACTGGGAGGAGGGCAACTACCGCAACCG
CGACGCCAACGACCCGGCCATCGGGATGCGGCGCGGCGAGATCCTGATCG
GTGGGCCCGCCGTCTGCCTCGGCTACTACGTGAACGAGCGCGCGCCCGAC
GCGGACGTGGTGAAGCGCAACGCGGAGGACTTTGTGACGATCAACGGCAT
GCGCTTCTTCTGCTCGGGCGACATCGGCCAGATCACGCCGAGCGGCTGCG
TGCAGATTATCGACCGGAAGAAGGACCTCGTCAAGCTGCAGCAGGGCGAG
TACGTCGCGCTCTCCAAGGTGGAGAACGCGCTCAAGAACTCGTCGTACAC
GCAGATCCCGTACGTCTACGCGCTCTCATCCAAGAGCTACTGCATCGCGC
TCCTCTGCCCGCAGCACGCGGCGATCCGCCAGCTCGCCGCCTCGCTGCAG
ATCAGCGGCAAGGAGCTTTCCGAGCTGTGCGCGCACCCGCAGATCGTCGC
GGCCGTGCTCAAGGACCTGCAGGCGCAGTGCAAGGCGGCCAAGCTCGCGG
GCTTCGAGACGCCGAGCAAGCTCATCCTCGTGTCGGACGAGTGGACCGTT
GAGAATGACATGCTCACCACGACGATGAAGATCAAGCGCAAGCCAATCGC
TGACCGGCACGCGAGCGAGATCAAGGCCGTTTACGTCTGAGCCCGCGCCT
TTTTGTACAACCTCGAGAGCGCCACTGTCTTGATGGCGCGCGCGTGCTGT
TGTGCAGGCCGTCGGCATTGACCGCGGCGCTTGAACGCAAGGCAGGCGCA
AGGCGCGGGAGGGATTGCTGGGGATGGCGGCTGCCGCAGTTGCTGAGCAG
AAGGCAGTCTCCGGCTCTCGACAGGTGGCGCCCGTTGTGCAGAATGTTCG
CAGCCCCTCCCCCCTCGGGCGGCTGCCATTCGGGGCAGCGCTCGCACATG
TGCTGCGCTCCGCAGCCGCACGCCACGGCCACCAACGCGTGTGCCTGCCG
TCACGCGCCGCGCCCGTGGGAACGACCGTTGCCCTCGCAC
```

```
GCACGAGGGCTCGACCTACTGCCCGCGCTGCGCGGCAAGATGCGCTGGCT
CGCGGCGAGCGTGCTCTTTCGGCTTCCCATCGTGCGCGAGCTCACCCTTT
GGACCGGCTGCATCGACGCGCGCCGCTCGGTTGCCGAGAGTGCGCTGCGT
GGCGGCTACTCAGTCGGCGTACTGCCCGGCGGCGAGCAGGAGCAGCTGCG
CACGCGCTACGGGCGCGAGTCGGTATATTTGCGCAAGCGCTTTGGCTTCG
TCAAGCTTGCGCTCCGCTTCGGCGTGCCGCTCGTGCCTGGGTACGTGTTC
GGGTGCGTCGACCTGTACCACACTTCATCCCTGCTCTTCTCGGCGCGCGA
GTGGCTCGTGCGCTCTCTCGGCGTGTGCGTGCCCGTGTGCTTCGGAGCGT
GGGGCGTGCCCATGGCGCCGCTTGCTGTGCCGCTCAACGTCGTGATCGGC
CGGCCGATCAAGCTGCCGCGCAACCCTGAGCCGACCGATGAGGACGTCGC
GCGCGCGCTCGACCAGTACATCGCCGCGCTGCGCGCGCTCTTTGACGAGA
ACAAGGCGCGCTTTGGCTATGCCGACCGCGAGCTGGAGGTGTGCTGATTG
TGAAGAAGTGTCATTGAAGGTCGGCGTCAGCAGGCGCACCGCGCACCAAG
CCACTCACGTCTTGATCGCTGAACCGCCGTGAACGATGCCGTTGCGACAC
GCTTGAAGATGGCCAGAAAAAAAAAAAAAAAA
```

ACTGCGTGTACACAGCATGGCGGCTCGCGCGGTTGACGCGCTCGTCGTGAGCGCGTTCAC
GGCGTTCGTGCAGATCGGCGTGTGGGCGCTCACGCCCGTGGGCATTGCGTGGGCCCTCGC
GTTCCACTGGAAGGTGACGCTGCCGCTGCTCGCCCTTTATCTCGCGTCGTACCTCGACGG
CGCCGAGGTGCGCGTCAAGCGCGTGCGCGCGTGGCCGGCGTTCTCCCGGCATTTTTGGCT
GTTCACGTTCATGCGCAGGGTCTACCGGCAGCGCGTTCACGTGCCAGCTGGCCTCGAGGC
CGAGGAGCAGATCATCCTAGCGCTGCATCCGCACGGCTCGATGGCGGACTACCGCGCGAT
CCTCGACGGCCAGCTGCTCGACCTACTGCCCGCGCTGCGCGGCAAGATGCGCTGGCTCGC
GGCGAGCGTGCTCTTTCGGCTTCCCATCGTGCGCGAGCTCACCCTTTGGACCGGCTGCAT
CGACGCGCGCCGCTCGGTTGCCGAGAGTGCGCTGCGTGGCGGCTACTCAGTCGGCGTACT
GCCCGGCGGCGAGCAGGAGCAGCTGCGCACGCGCTACGGGCGCGAGTCGGTATATTTGCG
CAAGCGCTTTGGCTTCGTCAAGCTTGCGCTCCGCTTCGGCGTGCCGCTCGTGCCTGGGTA
CGTGTTCGGGTGCGTCGACCTGTACCACACTTCATCCCTGCTCTTCTCGGCGCGCGAGTG
GCTCGTGCGCTCTCTCGGCGTGTGCGTGCCCGTGTGCTTCGGAGCGTGGGGCGTGCCCAT
GGCGCCGCTTGCTGTGCCGCTCAACGTCGTGATCGGCCGGCCGATCAAGCTGCCGCGCAA
CCCTGAGCCGACCGATGAGGACGTCGCGCGCGCGCTCGACCAGTACATCGCCGCGCTGCG
CGCGCTCTTTGACGAGAACAAGGCGCGCTTTGGCTATGCCGACCGCGAGCTGGAGGTGTG
CTGATTGTGAAGAAGTGTCATTGAAGGTCGGCGTCAGCAGGCGCACCGCGCACCAAGCCA
CTCACGTCTTGATCGCTGAACCGCCGTGAACGATGCCGTTGCGACACGCTTGAAGATGGC
CAGAAAAAAAAAAAAAAAA

Figure 7d

```
MAARAVDALV VSAFTAFVQI GVWALTPVGI AWALAFHWKV TLPLLALYLA SYLDGAEVRV
KRVRAWPAFS RHFWLFTFMR RVYRQRVHVP AGLEAEEQII LALHPHGSMA DYRAILDGQL
LDLLPALRGK MRWLAASVLF RLPIVRELTL WTGCIDARRS VAESALRGGY SVGVLPGGEQ
EQLRTRYGRE SVYLRKRFGF VKLALRFGVP LVPGYVFGCV DLYHTSSLLF SAREWLVRSL
GVCVPVCFGA WGVPMAPLAV PLNVVIGRPI KLPRNPEPTD EDVARALDQY IAALRALFDE
NKARFGYADR ELEVC
```

Figure 8a

GGCACGAGGGGGAGATGGCGGCGCCGACATCGCCGTACGGCGCGGAATCGCCGCGCGCGGCGTACGCGTAC
CCGGAGCGTGCAAATGTCAAGATGTCCGAGGCGCTGCGCGTACTCGACGAGGGCGTGCACCCGCTCGTTAT
TCACAGCTCGCAGATCCTCGCCGCCGCGCTGCTCGTCACGGCCGCCGTCAACCACTTTCCCAAGATCACCG
TCGCGGACCTCGCCGAGATCTGGCGCTCGCTGCAGATCGACGTGGCGTACGCGTTCGCGCTGACTGCGGTG
GCCGTGCTGCTTCTCGGCTACTACGCTCTCCGCCACCCGCGCCCCGTCTACCTCGTCGACTTCGCCACGTG
GCAGCTGCGCGACGACAAGGACGACGGCAGCCTGAGTGCGACGAGCGATTTCTTCCGCTCGACGATCACGG
ATTGCGGCAATTTTTGCGACGAGTCGGTCGACTTCCAGATGAAGCTTTTTGAGCGCAACCAGATCTCCGAG
CGCTGCTACTTCCCACCTGGCATCCGCGCCTACCGCAAGGGCGAGCGCGACTTTGACTTTTCGATGGCCGC
CGCGCGCAAGGAGTTCGAGACTGTCGTCTTCACGACCGTCGACGAGCTGCTCGCCAAGACGGGCGTAAAGC
CGCGAGATATCGACATCCTCGTCGTCAACTGCTCGCTCTTCAACCCGACGCCATCGCTGGCTGCGATCGTG
ATCAACCACTACCAGATGAAGGACTCCGTACAGAGCTACTCACTTGGCGGGATGGGTTGCTCAGCGGGACT
CATCTCAATCCACCTCGCAAAGGACCTGCTGCAGGTCTACCCGCGCAAGCGCGCGCTCGTCATCTCGACGG
AGAACATCACGCAAAATTTTTACCAGGGCAACGAAAAGTCGATGCTCATCTCGAACACGCTCTTCCGAATG
GGCGGCGCCGCCGTCCTCCTCTCCGGCCGCCACGCCGACCGGCGCGTCGCCAAGTATCAACTGCTGCACAC
CGTCCGCACGCACAAGGGCGCGGACCCGGACGCGTACCGGTGCGTCTTCCAGGAGGAGGACAAGGCGGGGC
ACGTGGGCGTGCGCCTGTCGAAAGACGTGATGGAGTGCGCCGGCGCCGCGATGAAGACCAACATCTCCGTC
CTCGCGCCTCTGATTCTGCCCGTTTCTGAGCAGGTCCGATTTCTCGCAAACTACGTTGCGCGCAAGTGGCT
GCGAATGAAAGGCGTGAAGGGATACGTGCCGGACTTCACAACGGCCGTGCAGCACTTTTGCATCCACACGG
GCGGGCGCGCGGTGCTCGACGCGCTGCAGGCGAACTTGTCGCTCTCAGATTACTACCTCGAGCCGAGCCGT
TACTCCCTGTGGCGCTGGGGTAACGTCTCAAGCGCCTCAGTCTGGTACGAGCTCGACTGGCTCGAAAAGTC
CGGCCGCATCCGGCGGGGCGACAAGGTGTGGCAGATTGGGTTTGGCAGCGGCTTCAAGTGCAACTCGGCCG
TCTGGCGGGCGTGCCGAGCGATGCCCTAGCTACGCCGGCGCCGTCCGCATTGCCAGTGGTTCGTGACAGAC
AGTCACACTGACGAGTGCGGAGTGACGTCTGACGCCTTCCCCCCCCCGCCCACCACCTCCACCTCCACCTC
CTTCACTCTCACTCAATCGCGCGGCGGCCAGAGCAGGAGCGCGCTCGTGCTCGCCATCACCGCCTTGTAGT
CCTCGCGCCGCTCGAGCGAGCGCGCGTCCATGAGCGGCACGGACGCGAAGCGGAAGAAGAGCCACATCACA
GCAGAAAAAAAAAAAAAAAAAAACTCGAGACTAGTTCTCTCTACCGCGCTGCCGAGCTCAAGCACGGCCGC
GTGTGCATGCTCGCCGTCACCGGCATGCTTGTCCAGGAGGTGTACTCGTGGCCGGCACCCGACGGCGTCTT
CAAGGCGCCGACGCCGCTCGGCGCGCTCTCGACCGTGCCGGCGCTCGGCCTCATCCAGCTCATCGTCTTCC
TCGGCATCATCGAGGTGCGCTCGGCGAACTACCAGGGCCGCGTGCCCGGCGACCTTGGCTTTGACCCGCTC
GG

Figure 8b

```
MAAPTSPYGA ESPRAAYAYP ERANVKMSEA LRVLDEGVHP LVIHSSQILA AALLVTAAVN
HFPKITVADL AEIWRSLQID VAYAFALTAV AVLLLGYYAL RHPRPVYLVD FATWQLRDDK
DDGSLSATSD FFRSTITDCG NFCDESVDFQ MKLFERNQIS ERCYFPPGIR AYRKGERDFD
FSMAAARKEF ETVVFTTVDE LLAKTGVKPR DIDILVVNCS LFNPTPSLAA IVINHYQMKD
SVQSYSLGGM GCSAGLISIH LAKDLLQVYP RKRALVISTE NITQNFYQGN EKSMLISNTL
FRMGGAAVLL SGRHADRRVA KYQLLHTVRT HKGADPDAYR CVFQEEDKAG HVGVRLSKDV
MECAGAAMKT NISVLAPLIL PVSEQVRFLA NYVARKWLRM KGVKGYVPDF TTAVQHFCIH
TGGRAVLDAL QANLSLSDYY LEPSRYSLWR WGNVSSASVW YELDWLEKSG RIRRGDKVWQ
IGFGSGFKCN SAVWRACRAM P
```

TRANSGENIC PLANTS EXPRESSING ENZYMES INVOLVED IN FATTY ACID BIOSYNTHESIS

This is the U.S. National Stage of International Application No. PCT/GB03/01099, filed Mar. 17, 2003 (published in English under PCT Article 21(2)), which in turn claims the benefit of Great Britain Application No. 0206308.9, filed Mar. 16, 2002, Great Britain Application No. 0212133.3, filed May 25, 2002, Great Britain Application No. 0216013.3 filed Jul. 11, 2002, and Great Britain Application No. 0225489.4 filed Nov. 1, 2002.

The invention relates to nucleic acid molecules which comprise nucleic acid sequences which encode enzymes involved in the biosynthesis of n-3 fatty acids, particularly docosahexanoic acid, or variants thereof; polypeptides encoded by said nucleic acids; cells transfected with said nucleic acid sequences and products comprising said nucleic acid sequences, polypeptides and/or cells.

DHA, an example of a n-3 fatty acid can be obtained directly from the diet or derived from metabolism of dietary linoleic and α-linolenic acid. To obtain sufficient amounts of this fatty acid humans have to eat foods rich in DHA. Currently the principle dietary source of DHA is fish or fish oil. However, this has many inherent problems; fish accumulate pollutants, the extracted oil has an unpleasant odour, there is a difficulty in controlling the proportion of specific desirable fatty acids from this source and since fish are a declining resource the market demand for DHA is not being met. Also, vegetarians do not have an obvious alternative food source to fish and therefore either do without DHA or have to take pure supplements.

Long chain polyunsaturated fatty acids (LPUFAs) are derived from the essential fatty acids (EFA) linoleic acid (18:2n-6) and α-linolenic acid (18:3n-3), the parent compounds of the so-called omega-3 and omega-6 EFA families by an alternating series of desaturation and elongation reactions (Haag, 2001), see FIG. 4. The major metabolite product of the n-6 pathway in mammals is arachidonic acid (AA) (20:4n-6), whilst the major end products of the n-3 pathway are eicosapentaenoic acid (EPA) (20:5n-3) and docosahexaenoic acid (DHA, 22:6n-3). The biosynthesis of 18:3n-3 from 18:4n-3 involves the action of a Δ6 desaturase (Horrobin D F, 1992). This is followed by an elongation reaction to 20:4n-3 (Sprecher et al., 1995) and a Δ5 desaturation to 20:5n-3 (Sprecher et al., 1995). The conventional view is that there is then a further elongation step converting 20:5n-3 to 22:5n-3, which is then followed by a final desaturation step involving the activity of a Δ4 desaturase to produce DHA (22:6n-3).

During evolution humans have consumed a diet containing approximately equal ratio of n-3 and n-6 essential fatty acids (1-2:1), but the last 100-150 years has seen a growing trend in Western diets towards the consumption of more n-6 fatty acids, resulting in an alteration of the ratio to 30:1 (Simonpolous, 1999). Whilst an increased intake of n-6 fatty acids is characterised by cardiovascular problems such as increased blood viscosity, vasospasm and vasoconstriction, the n-3 fatty acids are associated with health promoting properties. For example n-3 fatty acids have been described as anti-inflammatory, antithrombotic, antiarrhythmic, hypolipidemic and vasodilatory (Simonpolous, 1999). As such the role of DHA in the prevention and/or treatment of diseases such as coronary heart disease, hypertension, type II diabetes, ocular diseases, arthritis, cystic fibrosis and schizophrenia and has been the focus of a great deal of medical research.

The effect of n-3 polyunsaturated fatty acids in the cardiovascular diseases has shown that dietary intake of DHA can lower the risk of myocardial infarction, hypertension and complications associated with cardiac surgery. A number of population studies have correlated the dietary intake of DHA with cardiovascular risk factors. For instance, a study of a population of Inuits in Canada (426 subjects aged 18-74 yr), who traditionally consume large amounts of marine foods rich in n-3 fatty acids, showed that n-3 fatty acids, such as DHA were positively associated with HDL-cholesterol concentrations and inversely associated with triacylglycerol concentrations and the ratio of total to HDL cholesterol (Dewailly et al., 2001). It was concluded that the high dietary intake of n-3 fatty acids in the Inuit diet was probably responsible for the low mortality rate from ischemic heart disease in this population.

Essential fatty acids are structural components of all tissues and are indispensable for cell membrane synthesis. The brain, retina and other neural tissues have been found to be particularly rich in DHA, where it is involved in neural development and maturation of sensory systems (Uauy et al., 2000). A large body of research comparing infants fed with breast milk compared to formula milk, which is deficient in DHA and other omega 3-fatty acids, has concluded that the presence of DHA is critical during the development of the newborn (Horrocks et al., 1999). DHA forms 25% of the fatty acid complement of the glycosphingolipids of the brain and is an important component of the rods of the retina, and therefore a deficiency in DHA during infant development has been associated with a reduction in cognitive function and visual acuity. Furthermore, deficiencies in DHA have been associated with foetal alcohol syndrome, attention deficit hyperactivity disorder, cystic fibrosis, phenylketonuria and adrenoleukodystrophy.

To meet this increased demand for n-3 fatty acids such as DHA a number of approaches have been attempted. Methods to enhance the DHA content of meat by manipulating animal feed have been met with little success. The cultivation of marine micro-organisms such as the *Crypthecoclinium cohnii* and *Schizochytrium* sp, which are rich sources of DHA has also met with some limited success as the cultivation of algae is technically demanding and costly (Ashford et al., 2000).

There has been limited research focused on the identification of genes involved in the biosynthesis of n-3 fatty acids in algae. In one report the identification of a cDNA encoding a novel C18-$\Delta^9$ polyunsaturated fatty acid-specific elongating activity from the docosahexaenoic acid (DHA)-producing microalga, *Isochrysis galbana* was described (Qi et al., 2002). This 30 kDa elongase, designated IgASE1, shares only limited homology to animal and fungal proteins with elongating activity. When IgASE1 was expressed in the yeast *Saccharomyces cerevisiae*, it was shown to specifically elongate the C18-$\Delta^9$ polyunsaturated fatty acids, linoleic acid (C18:2n-6, $\Delta^{9,12}$ and alpha-linolenic acid (C18:3, $\Delta^{9,12,15}$), to eicosadienoic acid (C20:2, $\Delta^{11,14}$) and eicosatrienoic acid (C20:3 $\Delta^{11,14,17}$), respectively. It was concluded that a major route for eicosapentaenoic acid (C20:5 $\Delta^{5,8,11,14,17}$) and docosahexaenoic acid (C22:6 $\Delta^{4,7,10,13,16,19}$) syntheses in *I. galbana* may involve a $\Delta^8$ desaturation pathway. Δ6 and Δ5 desaturases are microsomal enzymes that are thought to be a component of a three-enzyme system that includes NADH-cytochrome $b_5$ reductase, cytochrome $b_5$, and the respective desaturase (Sprecher, 1981).

A number of Δ6 and Δ5 desaturases have been identified. In plants such as the herb, borage (*Borago officinalis*), the Δ6 desaturase has been identified (Sayanova et al., 1997). Δ6 and Δ5 desaturases have been identified in humans (Hyekyung et al., 1999 and Cho et al., 1999, respectively), in animals such as the nematode; *Caenorhabditis elegans* (Michaelson et al., 1998 and Napier et al., 1998) and in eukaryotic microorganisms such as the fungus *Mortierella alpina* (Huang et al., 1999 and Knutzon et al., 1998). In the human, Δ6 and Δ5 desaturase activities have been found in skeletal muscle, lung, placenta, kidney and pancreas, but are expressed at the highest levels in the liver, brain and heart (Hyekyung et al., 1999). In all these tissues however, Δ6 desaturase activity was found to be higher than that of Δ5 desaturase. The genes for both of the enzymes reside on chromosome 11, in a reverse orientation, being separated by <11,000 base pairs (Hyelyung et al., 1999). A Δ4 desaturase that can introduce a double bond at position 4 of 22:5 n-3 and 22:4 n-6 resulting in the production of DHA and docosapentanoic acid has been identified in the marine fungi *Thraustochytrium* sp (Qiu et al., 2001).

Cellular storage of fatty acids in triacylglycerol requires that the fatty acids are first activated to their acyl-CoA esters through the action of acyl-CoA synthetase enzyme. Acyl-CoA's are produced by acyl-CoA synthetase from fatty acid, ATP and Coenzyme A. Acyl-CoA synthetases can exhibit substrate specificity for different chain length or different degrees of saturation of the fatty acid. For example an arachidonate (20:4 n-6)-preferring acyl-CoA synthetase has been identified in rat (Kang et al., 1997). This enzyme has a high affinity for arachidonate and EPA and low affinity for palmitate. Several isoforms of acyl-CoA synthetases have also been identified in *Arabidopsis* (Schnurr et al., 2000).

Acyl CoA:diacyglycerol acyltransferase (DGAT) catalyses the final enzymatic step in the production of triacylglycerols in plants, fungi and mammals. The ezyme is responsible for transferring an acyl group from acyl-CoA to the sn-3 position of 1,2-diacylglycerol (DAG) to form triacylglycerol (TAG). The first cloning of a DGAT gene was from mouse (Cases et al., 1998). An *Arabidopsis* homologue of the mouse DGAT gene was subsequently reported and found to be present as a single copy gene (Hobbs et al., 1999). Jako et al., (2001) showed that the *Arabidopsis* Tag1 mutant which is disrupted in the DGAT gene and has a fatty acid and reduced oil phenotype can be complemented by expression of the DGAT cDNA. Jako et al., (2001) also showed that seed-specific over-expression of the DGAT cDNA in wild-type *Arabidopsis* enhances oil deposition and average seed weight thus confirming the important role of DGAT in regulating the quantity of seed triacylglycerols and the sink size in developing seeds. Protein purification based studies on the oleaginous fungus *Mortierella ramanniana* resulted in the identification of a second class of proteins involved in TAG production that are encoded by the DGAT2 gene family that are unrelated to the previously identified DGAT1 gene family (Lardizabal et al., 2001). A human homologue of the *Mortierella ramanniana* DGAT2 gene has been also been identified (Cases et al., 2001). Substrate specifities of the different families have yet to be determined.

Whilst higher plants do not typically biosynthesise LPUFAs such as DHA, they are an attractive target for genetic manipulation, particularly the low cost production of DHA in the vegetable oil of a crop such as oilseed rape. There have been no reports of higher plants that biosynthesise DHA, a number of attempts to introduce algal genes in order to manipulate the biosynthetic capacity of oil seed plants that produce LPUFAs have been reported. These have included the introduction of desaturases into transgenic plants to increase the production of DHA, EPA and also stearidonic acid (18:4n-3).

We herein disclose nucleic acid sequences which encode enzymes involved in n-3 fatty acid metabolism and the manipulation of these sequences and the biochemical pathways which comprise enzymes encoded by these sequences, to provide an alternative dietary source of n-3 fatty acids and, in particular, DHA. The sequences encode n-3 fatty acid elongase, desaturase, acyl CoA synthetase and diacylglycerol acyltransferase activities According to an aspect of the invention there is provided an isolated nucleic acid molecule comprising a DNA sequence selected from the group consisting of:
(i) the DNA sequence as represented in FIGS. 1*a*, 2*a*, 3*a*, 3*d*, 4*a*, 6*a*, 7*a*, 7*c* and 8*a*;
(ii) DNA sequences which hybridise to the sequence identified in (i) above; and
(iii) DNA sequences that are degenerate as a result of the genetic code to the DNA sequence defined in (i) and (ii)

In a preferred embodiment of the invention there is provided an isolated nucleic acid molecule which anneals under stringent hybridisation conditions to the sequences described in (i), (ii) and (iii) above.

Stringent hybridisation/washing conditions are well known in the art. For example, nucleic acid hybrids that are stable after washing in 0.1×SSC, 0.1% SDS at 60° C. It is well known in the art that optimal hybridisation conditions can be calculated if the sequence of the nucleic acid is known. Typically, hybridisation conditions uses 4-6×SSPE (20×SSPE contains 175.3 g NaCl, 88.2 g $NaH_2PO_4 \cdot H_2O$ and 7.4 g EDTA dissolved to 1 litre and the pH adjusted to 7.4); 5-10×Denhardts solution (50×Denhardts solution contains 5 g Ficoll (Type 400, Pharmacia), 5 g polyvinylpyrrolidone and 5 g bovine serum albumen); 100 μg-1.0 mg/ml sonicated salmon/herring DNA; 0.1-1.0% sodium dodecyl sulphate; optionally 40-60% deionised formamide. Hybridisation temperature will vary depending on the GC content of the nucleic acid target sequence but will typically be between 42-65° C.

In a preferred embodiment of the invention said nucleic acid molecules are isolated from an algal species.

Preferably said algal species is selected from the group consisting of: *Amphidinium carterae, Amphiphora hyalina, Amphiphora* sp., *Chaetoceros gracilis, Coscinodiscus* sp., *Crypthecodinium cohnii, Cryptomonas* sp., *Cylindrotheca fusiformis, Haslea ostrearia, Isochrysis galbana, Nannochloropsis oculata, Navicula* sp., *Nitzschia closterium, Pavlova lutheri, Phaeodactylum tricornutum, Prorocentrum minimum, Rhizosolenia setigera, Skeletonema costatum, Skeletonema* sp., *Tetraselmis tetrathele, Thalassiosira nitzschioides, Thalassiosira heterophorma, Thalassiosira pseudonana, Thalassiosira stellaris*.

According to a further aspect of the invention there is provided a polypeptide encoded by a nucleic acid molecule according to the invention.

In a preferred embodiment of the invention said polypeptide is a variant polypeptide and comprises the amino acid sequence represented in FIGS. 1*b*, 2*b*, 3*b*, 3*c*, 4*b*, 6*b*, 7*b*, 7*d*, or 8*b* which sequence has been modified by deletion, addition or substitution of at least one amino acid residue wherein said modification enhances the enzyme activity of said polypeptide.

A variant polypeptide may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and aspartic acid; c) asparagine and glutamine d) arginine and lysine; e) isoleucine, leucine, methionine and valine and f) phenylalanine, tyrosine and tryptophan. Most highly preferred are variants which retain or enhance the same biological function and activity as the reference polypeptide from which it varies.

A functionally equivalent polypeptide(s) according to the invention is a variant wherein one in which one or more amino acid residues are substituted with conserved or non-conserved amino acid residues, or one in which one or more amino acid residues includes a substituent group. Conservative substitutions are the replacements, one for another, among the aliphatic amino acids Ala, Val, Leu and Ile; interchange of the hydroxyl residues Ser and Thr; exchange of the acidic residues Asp and Glu; substitution between amide residues Asn and Gln; exchange of the basic residues Lys and Arg; and replacements among aromatic residues Phe and Tyr.

In addition, the invention features polypeptide sequences having at least 75% identity with the polypeptide sequences as herein disclosed, or fragments and functionally equivalent polypeptides thereof. In one embodiment, the polypeptides have at least 85% identity, more preferably at least 90% identity, even more preferably at least 95% identity, still more preferably at least 97% identity, and most preferably at least 99% identity with the amino acid sequences illustrated herein.

Ideally said modified polypeptide has enhanced fatty acid elongase, desaturase, acyl-CoA synthetase or diacylglycerol acyltransferase activity.

In a further preferred embodiment of the invention said polypeptide comprises the amino acid sequence represented in FIGS. 2*b*, 3*b*, 3*c*, 4*b*, 6*b*, 7*b*, 7*d*, 8*b*. Preferably said polypeptide consists of the amino acid sequence represented in FIGS. 2*b*, 3*b*, 3*c*, 4*b*, 6*b*, 7*b*, 7*d*, 8*b*.

According to a further aspect of the invention there is provided a vector including at least one nucleic acid according to the invention.

A vector including nucleic acid (s) according to the invention need not include a promoter or other regulatory sequence, particularly if the vector is to be used to introduce the nucleic acid into cells for recombination into the genome for stable transfection.

Preferably the nucleic acid in the vector is operably linked to an appropriate promoter or other regulatory elements for transcription in a host cell such as a prokaryotic, (e.g. bacterial), or eukaryotic (e.g. fungal, plant, mammalian or insect cell). The vector may be a bi-functional expression vector which functions in multiple hosts. In the example of nucleic acids encoding polypeptides according to the invention this may contain its native promoter or other regulatory elements and in the case of cDNA this may be under the control of an appropriate promoter or other regulatory elements for expression in the host cell.

By "promoter" is meant a nucleotide sequence upstream from the transcriptional initiation site and which contains all the regulatory regions required for transcription. Suitable promoters include constitutive, tissue-specific, inducible, developmental or other promoters for expression in plant cells comprised in plants depending on design. Such promoters include viral, fungal, bacterial, animal and plant-derived promoters capable of functioning in plant cells.

Constitutive promoters include, for example CaMV 35S promoter (Odell et al (1985) Nature 313, 9810-812); rice actin (McElroy et al (1990) Plant Cell 2: 163-171); ubiquitin (Christian et al. (1989) Plant Mol. Biol. 18 (675-689); pEMU (Last et al (1991) Theor Appl. Genet. 81: 581-588); MAS (Velten et al (1984) EMBO J. 3. 2723-2730); ALS promoter (U.S. application Ser. No. 08/409,297), and the like. Other constitutive promoters include those in U.S. Pat. Nos. 5,608, 149; 5,608,144; 5,604,121; 5,569,597; 5,466,785; 5,399,680, 5,268,463; and 5,608,142.

Chemical-regulated promoters can be used to modulate the expression of a gene in a plant through the application of an exogenous chemical regulator. Depending upon the objective, the promoter may be a chemical-inducible promoter, where application of the chemical induced gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al (1991) Proc. Natl. Acad. Sci. USA 88: 10421-10425 and McNellie et al. (1998) Plant J. 14(2): 247-257) and tetracycline-inducible and tetracycline-repressible promoters (see, for example, Gatz et al. (1991) Mol. Gen. Genet. 227: 229-237, and U.S. Pat. Nos. 5,814,618 and 5,789,156, herein incorporated by reference.

Where enhanced expression in particular tissues is desired, tissue-specific promoters can be utilised. Tissue-specific promoters include those described by Yamamoto et al. (1997) Plant J. 12(2): 255-265; Kawamata et al (1997) Plant Cell Physiol. 38(7): 792-803; Hansen et al (1997) Mol. Gen. Genet. 254(3): 337-343; Russell et al. (1997) Transgenic Res. 6(2): 157-168; Rinehart et al (1996) Plant Physiol. 112(3): 1331-1341; Van Camp et al (1996) Plant Physiol. 112(2): 525-535; Canevascni et al (1996) Plant Physiol. 112(2): 513-524; Yamamoto et al (1994) Plant Cell Physiol. 35(5): 773-778; Lam (1994) Results Probl. Cell Differ. 20: 181-196; Orozco et al (1993) Plant Mol. Biol. 23(6): 1129-1138; Mutsuoka et al (1993) Proc. Natl. Acad. Sci. USA 90(20): 9586-9590; and Guevara-Garcia et al (1993) Plant J. 4(3): 495-50.

In a preferred embodiment of the invention said tissue specific promoter is a promoter which is active during the accumulation of oil in developing oil seeds, see Broun et al. (1998) Plant J. 13(2): 201-210.

"Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment the promoter is an inducible promoter or a developmentally regulated promoter.

Particular vectors are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed) Oxford, BIOS Scientific Publishers, pp 121-148. Suitable vectors may include plant viral-derived vectors (see e.g. EP-A-194809).

Vectors may also include selectable genetic marker such as those that confer selectable phenotypes such as resistance to herbicides (e.g. kanamycin, hygromycin, phosphinotricin, chlorsulfuron, methotrexate, gentamycin, spectinomycin, imidazolinones and glyphosate).

Alternatively, or in addition, said vectors are vectors suitable for mammalian cell transfection or yeast cell transfection. In the latter example multi-copy vectors such as 2μ episomal vectors are preferred. Alternatively yeast CEN vectors and intergrating vectors such as YIP vectors are suitable for transformation of yeast species such as *Saccharomyces cerevisiae* and *Pichia* spp.

It will be apparent to one skilled in the art that a vector according to the invention may include nucleic acid molecules encoding different enzyme activities to facilitate the delivery of different enzyme activities to a transfected or transformed cell to reconstitute enzymic pathways.

According to a further aspect of the invention there is provided a cell transfected or transformed with at least one nucleic acid molecule or vector according to the invention.

Preferably said cell is transformed or transfected with at least two nucleic acid molecules according to the invention. Preferably still said cell is transformed with at least three nucleic acid molecules according to the invention, more preferably still, four nucleic acid molecules.

In a further preferred embodiment of the invention said cell is transformed with nucleic acid molecules encoding elongase, desaturase, acyl-CoA synthetase and diacylglycerol acyltransferase activities to provide a cell in which at least part of a 3-n fatty acid biosynthetic pathway is reconstituted.

In a yet further preferred embodiment of the invention said nucleic acid molecules are those molecules disclosed herein. In particular nucleic acid molecules which comprise the sequences as represented by FIGS. 1*a*, 2*a*, 3*a*, 3*d*, 4*a*, 6*a*, 7*a*, 7*c* and 8*a* and including a nucleic acid molecule which encodes a desaturase as represented by the amino acid sequence presented in FIG. 5, Tsp FAD4.

In a preferred embodiment of the invention said cell is selected from the group consisting of: mammalian cells (e.g Chinese Hamster Ovary cells); yeast cells (e.g. *Saccharomyces* spp, *Pichia* spp); algal cells (e.g *Phaeodactylum tricornutum, Chlamydomonas reinhardtii*); plant cells.

In a preferred embodiment of the invention said cell is a plant cell.

According to a further aspect of the invention there is provided a plant comprising a cell according to the invention.

In a preferred embodiment of the invention said plant is selected from: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolor, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Iopmoea batatus*), cassava (*Manihot esculenta*), coffee (*Cofea* spp.), coconut (*Cocos nucifera*), pineapple (*Anana comosus*), citris tree (*Citrus* spp.) cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Preferably, plants of the present invention are crop plants (for example, cereals and pulses, maize, wheat, potatoes, tapioca, rice, sorghum, millet, cassava, barley, pea), and other root, tuber or seed crops. Important seed crops are oil-seed rape, sugar beet, maize, sunflower, soybean, sorghum, and flax (linseed). Horticultural plants to which the present invention may be applied may include lettuce, endive, and vegetable brassicas including cabbage, broccoli, and cauliflower. The present invention may be applied in tobacco, cucurbits, carrot, strawberry, sunflower, tomato, pepper.

Grain plants that provide seeds of interest include oil-seed plants and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava been, lentils, chickpea, etc.

It will be apparent that transgenic plants adapted for the production of n-3 fatty acids, in particular DHA, can either be eaten directly or used as a source for the extraction of essential fatty acid, of which DHA would be a constituent.

According to a yet further aspect of the invention there is provided a seed comprising a cell according to the invention.

In a further preferred embodiment of the invention said cell is a yeast cell, preferably of the genus *Saccharomyces* spp, preferably Brewer's yeast *Saccharomyces cerevisiae*.

The genus *Saccharomyces* spp is used in both brewing of beer and wine making and also as an agent in baking, particularly bread. Yeast is a major constituent of vegetable extracts of which Marmite™ is a typical example. Yeast is also used as an additive in animal feed. It will be apparent that genetically engineered yeast strains can be provided which are adapted to synthesise n-3 fatty acids. These yeast strains can then be used in food stuffs and in wine and beer making to provide products which have enhanced n-3 fatty acid content and in particular DHA content.

According to a further aspect of the invention there is provided a foodstuff product comprising a yeast cell according to the invention.

In a preferred embodiment of the invention said foodstuff product is selected from the group consisting of: wine; beer; bread, baking products (e.g. bread, cake); vegetable extracts.

In a further preferred embodiment of the invention said wine or beer in non-alcoholic.

According to a further aspect of the invention there is provided a fermentation process comprising a yeast cell according to the invention.

In a preferred embodiment of the invention said fermentation process comprises the steps of:
i) providing a vessel containing a yeast cell according to the invention and constituents required for fermentation and fatty acid biosynthesis; and
ii) providing conditions conducive to the fermentation of the liquid composition contained in said vessel.

According to a yet further aspect of the invention there is provided an animal feed product comprising a cell according to the invention.

In a preferred embodiment of the invention said cell is a plant cell or yeast cell.

According to a further aspect of the invention there is provided a method of modulating the level of n-3 fatty acid, in particular DHA, or variants thereof, in a plant cell comprising;
i) providing a plant cell according to the invention;
ii) regenerating the plant cell into a plant; and
iii) monitoring n-3 fatty acid production by said plant.

According to a further aspect of the invention there is provided a method for the production and optionally the extraction of n-3 fatty acids, in particular DHA, comprising:
i) providing a cell according to the invention;
ii) providing conditions conducive to the growth of said cell; and
iii) extracting n-3 fatty acids, or variants thereof, from said cell.

According to a yet further aspect of the invention there is provided a method for the production and optionally the extraction of n-3 fatty acid, particularly DHA, comprising:

i) providing a plant cell according to the invention;
ii) regenerating said cell into a plant; and
iii) extracting n-3 fatty acids, or variants thereof from said plant.

According to a further aspect of the invention there is provided n-3 fatty acids, particularly DHA, or variants thereof, obtainable by the method(s) according to the invention.

In a preferred embodiment of the invention said n-3 fatty acid, or variant thereof, is for use as a pharmaceutical.

In a further preferred embodiment of the invention said n-3 fatty acid, or variant thereof, is for use in the manufacture of a medicament for use in the treatment of conditions which would benefit from administration of n-3 fatty acids, or variant thereof.

In a preferred embodiment of the invention said condition is selected from the group consisting of: cardiac arrhythmia's; rheumatoid arthritis; Crohn's disease; schizophrenia; cancer; foetal alcohol syndrome; attention deficient hyperactivity disorder; cystic fibrosis; phenylketonuria; unipolar depression; aggressive hostility; adrenoleukodystophy; coronary heart disease, hypertension, type II diabetes, ocular diseases.

According to a further aspect of the invention there is provided a non-human transgenic animal comprising at least one nucleic acid molecule according to the invention.

According to a yet further aspect of the invention there is provided a reaction vessel comprising at least one polypeptide according to the invention, fatty acid substrates and co-factors characterised in that said vessel is adapted for the conversion of said fatty acids substrates to n-3 fatty acids, in particular docosahexaenoic acid.

In a preferred embodiment of the invention said vessel comprises polypeptides having elongase, desaturase, acyl-CoA synthetase and diacylglycerol acyltransferase activities to provide a vessel in which at least part of a 3-n fatty acid biosynthetic pathway is reconstituted.

In a further preferred embodiment of the invention said polypeptides are those protein molecules disclosed herein. In particular, protein molecules which comprise the sequences as represented by FIGS. 1b, 2b, 3b, 3c, 4b, 5, 6b, 7b, 7d and 8b.

In a preferred embodiment of the invention said at least one polypeptide is expressed by a cell according to the invention.

In a preferred embodiment of the invention said polypeptide(s) is/are soluble. Alternatively said polypeptide(s) is/are immobilised.

In a further preferred embodiment of the invention said vessel is a bioreactor.

It will be apparent to one skilled in the art that a polypeptide according to the invention has utility with respect to the in vivo biosynthesis of n-3 fatty acids through transformation or transfection of nucleic acids encoding said polypeptide(s) into suitable host cells. Fatty acids can then either be extracted from said cells or foods comprising said cells can be eaten. Cells expressing said polypeptide (s) can also be incubated under suitable growth conditions to facilitate the synthesis of fatty acids. Alternatively, said polypeptide (s) can either be purified from an algal cell culture or manufactured recombinantly and used in a bioreactor to synthesise fatty acids in vitro. It will also be apparent that the invention involves, inter alia, the reconstitution of at least part of an algal n-3 fatty acid biosynthetic pathway which, either in a cell or in vitro, provides for a source of n-3 fatty acids which is an alternative to either the exploitation of algae in bioreactors or the consumption of fish.

An embodiment of the invention will now be described by example only and with reference to the following figures:

Table 1 represents fatty acid analysis of P. lutheri cells at two stages of growth.

FIG. 1a represents the nucleic acid sequence of a nucleic acid molecule comprising a fatty acid elongase, PlELO1 (SEQ ID NO: 1); FIG. 1b the amino acid sequence comprising PlELO1 (SEQ ID NO: 2).

FIG. 2a represents the nucleic acid sequence of a nucleic acid molecule comprising a fatty acid elongase, PlELO2 (SEQ ID NO: 3); FIG. 2b the amino acid sequence comprising PlELO2 (SEQ ID NO: 4).

FIG. 3a represents the nucleic acid sequence of a nucleic acid molecule comprising fatty acid desaturase, PlDES1 (SEQ ID NO: 5); FIG. 3b the amino acid sequence comprising PlDES1 (SEQ ID NO: 6) FIG. 3c represents the full length amino acid sequence of PlDES1 (SEQ ID NO: 7); FIG. 3d represents the full length nucleic acid sequence of PlDES1 (SEQ ID NO: 8).

FIG. 4a represents the nucleic acid sequence of a nucleic acid molecule comprising fatty acid desaturase, PlDES2 (SEQ ID NO: 9); FIG. 4b the amino acid sequence comprising PlDES2 (SEQ ID NO: 10).

FIG. 5 represents a sequence comparison between the Pavlova lutheri proteins PlDES1 (SEQ ID NO: 6), PlDES2 (SEQ ID NO: 10), and the Thraustochytrrium sp protein FAD4 (SEQ JD NO: 11).

Figures 6A, 6B:
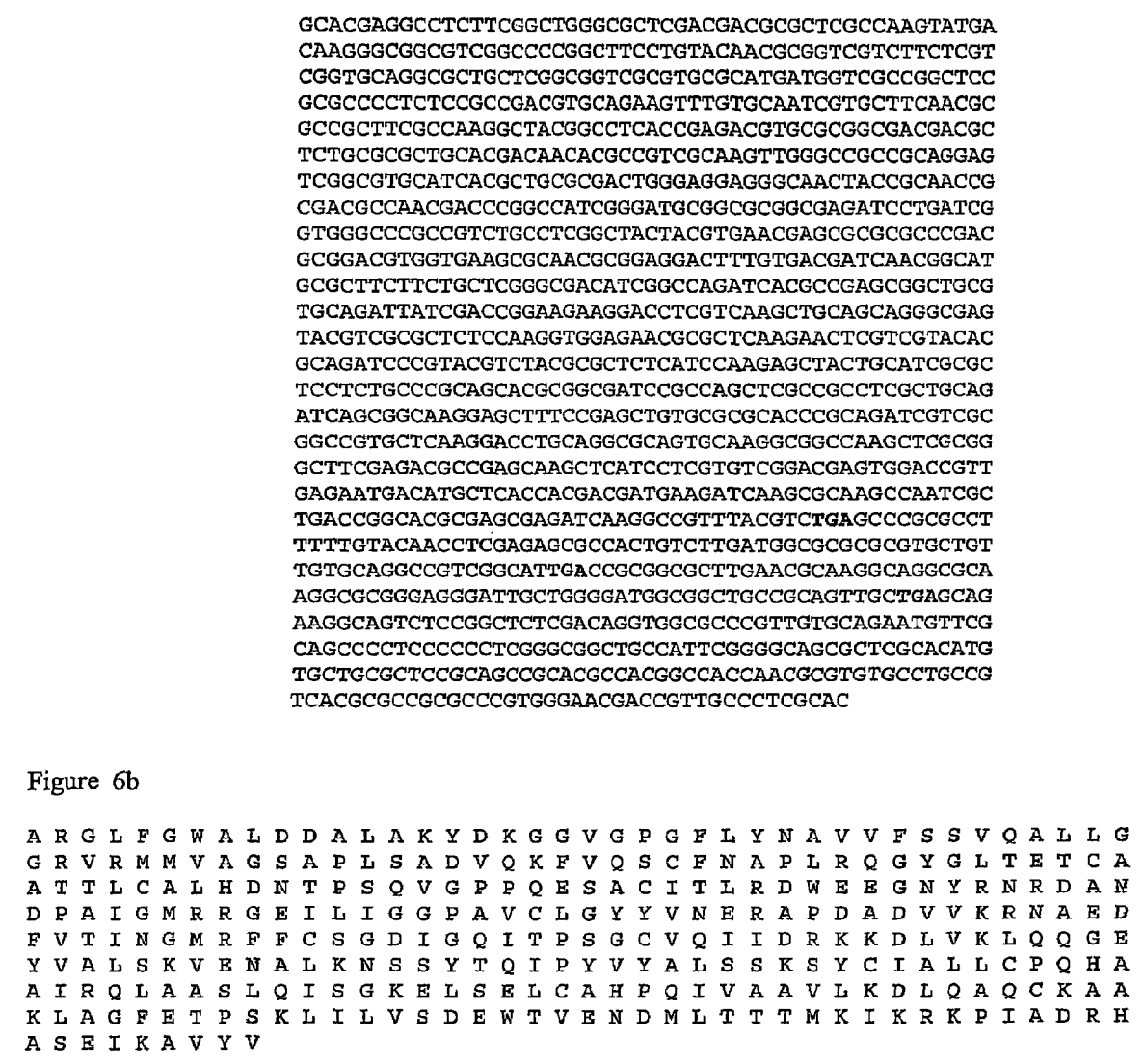

FIG. 6a represents the nucleic acid sequence of a nucleic acid molecule comprising acyl-CoA synthetase, PlACS1 (SEQ ID NO: 12); FIG. 6b the amino acid sequence comprising PlACS1 (SEQ ID NO: 13).

FIG. 7a represents the nucleic acid sequence of a nucleic acid molecule comprising diacyiglycerol acyltransferase, PlDGAT2-1 (SEQ ID NO: 14); FIG. 7b the amino acid sequence comprising PlDGAT2-1 (SEQ ID NO: 19); FIG. 7c the full length sequence of a nucleic acid molecule encoding PlDGAT2-1 (SEQ ID NO: 15); FIG. 7d the full length amino acid sequence of PlDGAT2-1 polypeptide (SEQ ID NO: 16).

FIG. 8a represents the nucleic acid sequence of a nucleic acid molecule comprising a fatty acid elongase, PlELO1 (SEQ ID NO: 17); FIG. 8b the amino acid sequence comprising PlELO1 (SEQ if) NO: 18).

MATERIALS AND METHODS

Cultivation of *Pavlova lutheri*

*Pavlova lutheri* (CCAP 931/1) was obtained from the Culture Collection of Algae and Protozoa (Dunstaffnage Marine Lab., Oban, PA34 4AD, Scotland, U.K.).

The growth medium used in all experiments was enriched artificial seawater medium (EASW), made up in 20 l batches as described by Harrison et al. (1980), and modified by Thompson et al. (1991). The medium was further modified by increasing the macronutrient concentrations of $NaNO_3$ and $Na_2SiO_3 \cdot 9H_2O$ to 1 mM, and $NaH_2PO_4$ to 200 µM. The silicate was dissolved separately in deionized distilled water and the pH adjusted to approximately 8.0 with 50% HCl before it was added to the medium. This medium was buffered to pH 8.0 by adding 20 mM N-[2-hydroxyethyl]piperazine-N'-[2-ethanesulfonic acid] (HEPES) and 20 mM NaOH. The freshly prepared medium was filtered through a 0.22 µM Millipore™ GS membrane filter into a 20 l sterile propylene reservoir. It was then dispatched by 0.5 l in 1 l conical glass flasks and sterilized by autoclaving (30 min, 120° C.). The batch cultures were grown at 15° C. with 50 µE m$^{-2}$ s$^{-1}$ constant illumination, and aeration provided by shaking the flasks at 150 rpm.

Cell density was monitored by counting cells with a haemacytometer. Since the *Pavlova lutheri* cells are motile, they were first incubated in sodium azide 20 mM to immobilise before counting.

The nitrate concentration was determined periodically during the culture time by measuring the change of the medium absorbance at 220 nm, according to the method described by Collos et al. (1999).

Isolation of Total and poly(A)⁺ RNA from *P. lutheri*

The algal culture was harvested by centrifugation at 4,500 rpm for 15 min. The cell pellet was suspended in 1 volume of extraction buffer (25 mM Tris-HCl pH 8.0, 25 mM EDTA pH 8.0, 75 mM NaCl, 1% SDS v/v, 7.8% β-mercaptoethanol v/v, in DEPC treated water), and one volume of 25:24:1 phenol:chloroform:isoamyl alcohol (v/v) was added. After 13,000 rpm centrifugation at 4° C. for 10 min, the aqueous phase was transferred to a new tube and 1 volume of 24:1 chloroform:isoamyl alcohol v/v added. After a second round of centrifugation, the upper phase was transferred to a fresh tube and LiCl added to a final concentration of 2 M. This solution was incubated for 1 hr at −20° C., and then centrifuged at 13,000 rpm at 4° C. for 15 min. The resulting pellet was re-suspended in DEPC treated water and the RNA was precipitated by addition of 0.1 volume of 3 M sodium acetate, pH 5.5 and 2.5 volumes of absolute ethanol followed by incubation for 20 min at 4° C. This sample was then centrifuged at 13,000 rpm at 4° C. for 15 min and the resulting pellet was washed with 70% ethanol, dried and re-suspended in DEPC treated water. Quantity and quality of the extract were estimated by measuring optical density at 260 and 280 nm (1 $O.D._{260\,nm}$=40 μg/ml RNA). An aliquot of the extract was also visualised on a 1% (w/v) agarose gel containing ethidium bromide.

For the cDNA library construction, poly(A)⁺ RNA was prepared with the Poly(A) Quick® mRNA isolation kit (Stratagene) from cells harvested during the exponential phase.

cDNA Library Construction and pBluescript Phagemid Excision

Double-stranded, end-adapted cDNA synthesised using a cDNA synthesis kit (Stratagene) was passed through a Sepharose CL-2B gel filtration column (Stratagene) to remove adapters and small cDNA molecules. cDNA eluted from the column was phenol-extracted, ethanol-precipitated and ligated to arms of the Uni-ZAP XR Vector (Stratagene) before packaging into λ phage using the Gigapack III Gold Packaging Extract (Stratagene). A primary library of 3×10⁶ plaque forming units (pfu) was obtained with the majority of the inserts examined ranging from 0.3 to 1.5 kb. The library was subsequently amplified.

After amplification, the cDNA library was excised using the ExAssis™ Interference-Resistant Helper Phage (Stratagene). The excised phagemids were plated as individual bacterial colonies following the manufacturer's instructions. The presence of insert was checked by PCR using universal primers and clones containing cDNA longer than 0.2 kb were selected for sequencing.

Sequencing and Sequence Analysis

Sequencing reactions were prepared with the ABI Prism Big Dye-Terminator cycle sequencing kit (PE Applied Biosystems), using the universal T3 primer, and these were run on an ABI3700 (96-capillaries) sequencer (PE Applied Biosystems). The resulting Expressed Sequence Tags (ESTs) were processed such that all vector sequences were removed and further examined using standard nucleotide sequence alignment algorithms in order to identify EST clones with overlapping sequences. These overlapping sequences were then assembled into contigs. These contigs were annotated by comparison with the non-redundant peptide and nucleotide databases available from the National Centre for Biotechnology Information (NCBI). The NCBI databases had been downloaded to a local Silicon Graphics Server which allowed the annotation of thousands of ESTs to be performed as a batch job using the BLAST 2 sequence alignment algorithm (Altschul et al., 1997).

The PlELO1 PlELO2, PlDES1, PlDES2, PlACS1 and PlDGAT2-1 clones were identified on the basis of homology with other fatty acid elongase/desaturase/acyl-CoA synthase or diacylglycerol acyltransferase genes in the NCBI nucleotide and protein databases.

Functional Analysis of the PlELO1 PlELO2, PlDES1, PlDES2, PlACS1 and PlDGAT2-1 ORFS by Heterologous Expression.

Functional characterisation of the amino acid sequence encoded by PlELO1 and PlELO2 will be performed under protocols previously described (Jaworski et al., 2001 (or refer to as: U.S. Pat. No. 6,307,128); Qi et al., 2002). To this aim, several species of fatty acid substrates will be considered: saturated (16:0, 18:0, 20:0, 22:0), monounsaturated (16:1, 18:1, 20:1) and polyunsaturated (20:4n-6, 20:5n-3, 22:5n-3) (FIG. 4).

Functional characterisation of the amino acid sequence encoded by PlDES1 and PlDES2 will be performed under protocols previously described (Qiu et al., 2001). To this aim, several species of fatty acid substrates will be considered: saturated (16:0, 18:0), monounsaturated (16:1, 18:1) and polyunsaturated (18:2n-6, 18:3n-3, 18:3n-6, 18:4n-3; 20:2n-6, 20:3n-3; 20:3n-6, 20:4n-3, 20:4n-6, 20:5n-3, 22:4n-6, 22:5n-3 and 22:5n-6).

Functional characterisation of the amino acid sequence encoded by PlACS1 will be performed under protocols previously described (Kang et al., 1997). To this aim, several species of fatty acid substrates will be considered: saturated (8:0, 10:0, 12:0, 16:0, 18:0, 20:0, 22:0), monounsaturated (14:1, 16:1, 18:1) and polyunsaturated (18:2n-6, 18:3n-3, 18:3n-6, 20:4n-6, 20:5n-3 and 22:6n-3).

Functional characterisation of the amino acid sequence encoded by PlDGAT2-1 will be performed under protocols previously described (Lardizabal et al., 2001; Cases et al., 2001, Zou et al., 1999). To this aim, DGAT activity will be assayed by incorporation of [1-$^{14}$C] diacylglycerol into TAG in the presence of several species of fatty acyl CoA substrates that are representative of fatty acids that partition to TAG in *P. lutheri*. These include: 14:0, 16:0, 16:1, 18:0, 18:1, 18:2, 18:4, 20:5 and 22:6.

TAG Extraction and Fatty Acids Analysis

The alga cells (2 ml of culture medium) were harvested during the experimental period by centrifugation at 13,000 rpm for 15 min. Fifty μg of tripentadecanoin (15:0-TAG) were added to the pellet as an internal standard. The pellet was then suspended in 1 ml of 2:1 chloroform:methanol (v/v) and frozen in liquid nitrogen. After 1 hour at 4° C., the cell debris was discarded by centrifugation and 0.3 ml of 0.9% KCl added to the supernatant. After centrifugation, the bottom phase was transferred into a 2 ml Ependorf and the KCl rinsed with 0.5 ml of chloroform. The chloroform phases were pooled and dried. The FA extract was suspended in 0.2 ml of hexane, and this volume was divided in 2 fractions of 0.1 ml. The first fraction was dried, and the lipid extract suspended in 0.2 ml of hexane. This represented the total lipid extract. The second fraction was used to isolate the TAGs by hydrophobic chromatography. Bond Elut (Varian) 1 ml solid phase extraction columns with 100 mg Si packing were used to partition TAGs from other lipids in algal extracts. This protocol was adapted from a method described by Yongmanitchai and Ward (1992). The eluate was dried and the TAG extract suspended in 0.2 ml of hexane. The products of these two extractions were analysed by GC as described previously by Larson and Graham (2001).

The same methodology will be employed to extract lipids and fatty acids from yeast cells in order to perform the functional analysis of PlELO1 PlELO2 and PlDES 1 following the feeding of different fatty acids as outlined above.

Fatty Acid Composition of *P. lutheri* Cells

Table 1: Fatty acid composition (molar %) of *P. lutheri* cells at two stages of growth.

The important point to note from the data presented in table 1 is that *P. lutheri* does not produce 20:0, 22:0, 24:0, 20:1, 22:1 fatty acids but does produce 20:5n-3 and 22:6n-3. The amino acid sequence derived from the PlELO1 gene as shown in FIG. 2 has closest homology with plant elongases that are involved in the production of saturated and monounsaturated C20 and C22 fatty acids. *P. lutheri* does not produce such fatty acids. Therefore we conclude that the PlELO1 gene product is involved in the production of 22:5 and 22:6 fatty acids which are found in *P. lutheri*.

Cloning and Characterization of the Genes PlELO1, PlELO2, PlDES 1, PlDES 2, PlACS1 and PlDGAT2-1

The first pass sequencing of 5,719 cDNA clones from a cDNA library prepared from *P. luthleri* resulted in the identification of 34 cDNA clones from a single gene which gives a predicted amino acid sequence that has significant identity with fatty acid elongase genes from a variety of organisms (FIG. 3). This abundance of copies of the elongase gene indicates that it is expressed at a significant level in *P. lutheri* cells that are producing DHA and provides further proof that the PlELO1 gene encodes an elongase 3-ketoacyl-CoA synthase polypeptide that catalyses the condensation of malonyl-CoA with acyl-CoA in the conversion of eicosapentaenoic acid to ω-docosapentaenoic acid which in turn is converted to docosahexaenoic acid.

Figures 2A, 2B:
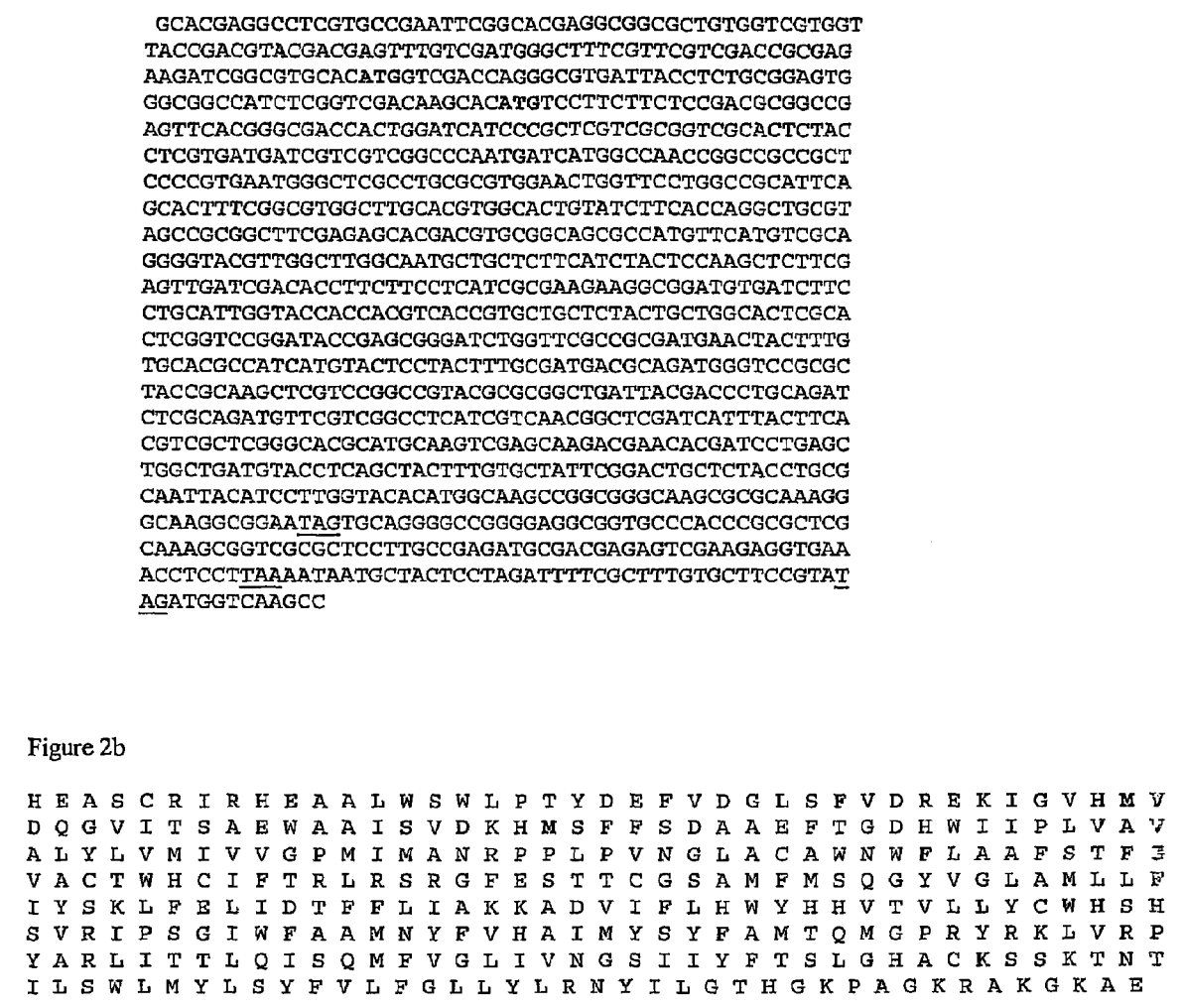

The sequencing of 5,719 cDNA clones from the *P. lutheri* library also resulted in the identification of six cDNA clones from a single gene which gives a predicted amino acid sequence that has significant identity with fatty acid desaturase genes from a variety of organisms (FIGS. 2a and 2b). This elongase gene has been designated PlELO2.

The sequencing of 5,719 cDNA clones from the *P. lutheri* library also resulted in the identification of four cDNA clones from a single gene which gives a predicted amino acid sequence that has significant identity with fatty acid desaturase genes from a variety of organisms FIGS. 3a, 3b, 3c and 3d). This desaturase gene has been designated PlDES 1.

The sequencing of 5,719 cDNA clones from the *P. lutheri* library also resulted in the identification of three cDNA clones from a single gene which gives a predicted amino acid sequence that has significant identity with fatty acid desaturase genes from a variety of organisms (FIGS. 4a and 4b). This desaturase gene has been designated PlDES 2.

The derived amino acid sequences from PlDES 1 and PlDES 2 both contain a histidine motif typical of fatty acid desaturase genes such as the Δ4 desaturase gene from the marine fungus *Thraustochytrium* sp. that is involved in the production of DHA and docosapentaenoic acid (Qiu et al., 2001) (FIG. 5).

The sequencing of 5,719 cDNA clones from the *P. lutheri* library also resulted in the identification of twelve cDNA clones from a single gene which gives a predicted amino acid sequence that has significant identity with acyl-CoA synthetase genes from a variety of organisms (FIGS. 6a and 6b). This acyl-CoA synthetase gene has been designated PlACS1.

The sequencing of 5,719 cDNA clones from the *P. litheri* library also resulted in the identification of one cDNA clone which gives a predicted amino acid sequence that has significant identity with diacylglycerol acyltransferase 2 genes from several organisms (FIGS. 7a and 7b). This diacylglycerol acyltransferase 2 gene has been designated PlDGAT2-1.

The full length cDNA and protein sequence of PlELO1 is disclosed in FIGS. 8a and 8b respectively.

REFERENCES

1. Uauy R, Mena P, Rojas C Essential fatty acids in early life: structural and functional role. Proc Nutr Soc February 2000; 59(1):3-15
2. Dewailly E, Blanchet C, Lemieux S, Sauve L, Gingras S, Ayotte P, Holub B J. n-3 Fatty acids and cardiovascular disease risk factors among the Inuit of Nunavik. Am J Clin Nutr October 2001; 74(4):464-73
3. Salem N et al. (1994) "Arachidonate and docosahexaenoate biosynthesis in various species and compartments in vivo." *World Review of Nutrition and Dietetics*, vol. 75, pp. 114-119.
4. Haag, M. Depressive Symptoms in Schizophrenia. The Medicine Journal, November 2001. Page 1-7.
5. Qi B, Beaudoin F, Fraser T, Stobart A K, Napier J A, Lazarus C M. Identification of a cDNA encoding a novel C18-Delta(9) polyunsaturated fatty acid-specific elongating activity from the docosahexaenoic acid (DHA)-producing microalga, Isochrysis galbana. FEBS Lett 2002 Jan. 16; 510(3):159-65
6. Ashford A, Barclay W R, Weaver C A, Giddings T H, Zeller S. Electron microscopy may reveal structure of docosahexaenoic acid-rich oil within Schizochytrium sp. Lipids December 2000; 35(12):1377-86
7. Hammond B G, Mayhew D A, Robinson K, Mast R W, Sander W J. Safety assessment of DHA-rich microalgae from *Schizochytrium* sp. Regul Toxicol Pharmacol June 2001; 33(3):356-62
8. Simonpolous A P. Essential fatty acids in health and chronic disease. Am. J. Clin. Nutr. 1999,7 0 (3); 560S-569S.
9. Horrocks L A & Yeo Y K. Health benefits of docosahexaenoic acid (DHA). Pharmacol. Res. 1999; 40(3):211-
10. Collos, Y., Mornet, F., Sciandra, A., Waser, N., Larson, A., Harrison, P. J., 1999. An optical method for the rapid measurement of micromolar levels of nitrate in marine phytoplankton cultures. Journal of Applied Phycology 11, 179-184.
11. Harrison, P. J., Waters, R. E., Taylor, F. J. R., 1980. A broad spectrum artificial seawater medium for coastal and open ocean phytoplankton. Journal of Phycology 16, 28-35.
12. Larson, T. R., Graham I. A., 2001. A novel technique for the sensitive quantification of acylCoA esters from plant tissues. The Plant Journal 25, 155-125.
13. Thompson, P. A., Harrison, P. J., Parslow, J. S., 1991. Influence of irradiance on cell volume and carbon quota for ten species of marine phytoplankton. Journal of Phycology 27, 351-360.
14. Yongmanitchai, W., Ward, O. P., 1992. Separation of lipid classes from *Phaeodactylum tricornutum* using silica cartridges. Phytochemistry 31, 3405-340.

Broun P, Boddupalli S. Somerville C. 1998. A bifunctional oleate 12-hydroxylase: desaturase from *Lesquerella fendleri*. Plant J 13(2): 201-10

Schnurr J A, Shockey J, Browse J. 2000 Characterization of an acyl-CoA synthetase from *Arabidopsis thaliana*. Biochem Soc Trans. December; 28(6):957-8.

Kang M J, Fujino T, Sasano H, Minekura H, Yabuki N, Nagura H, Iijima H, Yamamoto T T. 1997 A novel arachidonate-preferring acyl-CoA synthetase is present in steroidogenic cells of the rat adrenal, ovary, and testis. Proc Natl Acad Sci USA. April 1; 94(7):2880-4.

Qiu X, Hong H, MacKenzie S L. 2001 Identification of a Delta 4 fatty acid desaturase from *Thraustochytrium* sp. involved in the biosynthesis of docosahexanoic acid by heterologous expression in *Saccharomyces cerevisiae* and *Brassica juncea*. J Biol Chem. August 24; 276(34):31561-6.

Cases S, Smith S J, Zheng Y W, Myers H M, Lear S R, Sande E, Novak S, Collins C, Welch C B, Lusis A J, Erickson S K, Farese R V Jr. 1998. Identification of a gene encoding an acyl CoA:diacylglycerol acyltransferase, a key enzyme in triacylglycerol synthesis. Proc Natl Acad Sci USA. October 27; 95(22):13018-23.

Hobbs D H, Lu C, Hills M J. 1999. Cloning of a cDNA encoding diacylglycerol acyltransferase from *Arabidopsis thaliana* and its functional expression. FEBS Lett. 11; 452 (3): 145-9.

Jako C, Kumar A, Wei Y, Zou J, Barton D L, Giblin E M, Covello P S, Taylor D C. 2001. Seed-specific over-expression of an *Arabidopsis* cDNA encoding a diacylglycerol acyltransferase enhances seed oil content and seed weight. Plant Physiol. 126(2):861-74.

Lardizabal K D, Mai J T, Wagner N W, Wyrick A, Voelker T, Hawkins D J. 2001. DGAT2 is a new diacylglycerol acyltransferase gene family: purification, cloning, and expression in insect cells of two polypeptides from *Mortierella ramanniana* with diacylglycerol acyltransferase activity. J Biol Chem. 19; 276(42):38862-9.

Cases S, Stone S J, Zhou P, Yen E, Tow B, Lardizabal K D, Voelker T, Farese R V Jr. 2001. Cloning of DGAT2, a second mammalian diacylglycerol acyltransferase, and related family members. J Biol Chem. October 19; 276 (42):38870-6.

Zou J, Wei Y, Jako C, Kumar A, Selvaraj G, Taylor D C. 1999. The *Arabidopsis thaliana* TAG1 mutant has a mutation in a diacylglycerol acyltransferase gene. Plant J. 19(6):645-53.

TABLE 1

Fatty acid composition (molar %) of *P. lutheri* cells at different stages of the growth cycle. Each value represents the mean ± SD of two replicate from one flask.

| Fatty acids | Exponential phase | | Stationary phase | |
|---|---|---|---|---|
| | 189 h[a] | 285 h | 353 h | 452 h |
| In total extract | | | | |
| 14:0: | 12.19 ± 2.08 | 11.33 ± 0.44 | 11.07 ± 0.12 | 11.08 ± 0.03 |
| 16:0 | 26.05 ± 2.93 | 21.62 ± 0.61 | 16.40 ± 0.20 | 25.26 ± 0.17 |
| 16:1n-7 | 21.92 ± 3.60 | 23.78 ± 1.34 | 20.28 ± 0.29 | 27.56 ± 0.37 |
| 18:0 | 8.27 ± 0.90 | 3.48 ± 0.35 | 2.93 ± 0.13 | 1.39 ± 0.24 |
| 18:1n-9 | ND[b] | 0.93 ± 0.08 | 8.22 ± 0.12 | 2.32 ± 0.07 |
| 18:2n-6 | ND | 2.43 ± 0.15 | 2.33 ± 0.02 | 3.66 ± 0.03 |
| 18:3n-3 | ND | ND | ND | 0.38 ± 0.01 |
| 18:4n-3 | ND | 4.72 ± 0.20 | 5.81 ± 0.11 | 4.39 ± 0.03 |
| 20:3n-3 | ND | ND | ND | 0.27 ± 0.01 |
| 20:5n-3 | 13.94 ± 1.48 | 14.44 ± 0.73 | 15.21 ± 0.39 | 14.87 ± 0.23 |
| 22:6n-3 | 8.62 ± 1.74 | 7.90 ± 0.43 | 7.35 ± 0.15 | 5.89 ± 0.03 |
| In TAG extract | | | | |
| 14:0 | 11.93 ± 0.08 | 6.96 ± 0.66 | 6.83 ± 0.03 | 7.63 ± 0.18 |
| 16:0 | 43.04 ± 1.59 | 22.94 ± 0.76 | 20.16 ± 0.70 | 29.74 ± 0.95 |
| 16:1n-7 | 37.70 ± 2.23 | 33.52 ± 5.12 | 39.39 ± 3.10 | 37.40 ± 1.42 |
| 18:0 | ND | 1.52 ± 2.15 | 0.62 ± 0.87 | 0.91 ± 0.53 |
| 18:1n-9 | ND | 2.66 ± 2.28 | 0.60 ± 0:85 | 3.40 ± 0.10 |
| 18:2n-6 | ND | 7.93 ± 4.31 | 3.33 ± 1.66 | 6.15 ± 0.31 |
| 18:4n-3 | ND | ND | ND | 0.92 ± 0.16 |
| 20:5n-3 | 7.33 ± 0.73 | 6.02 ± 1.07 | 5.31 ± 0.16 | 8.50 ± 0.42 |
| 22:6n-3 | ND | 3.69 ± 0.91 | 3.31 ± 0.64 | 1.97 ± 0.07 |

[a]time of incubation.
[b]ND, Not detected.

The invention claimed is:

1. An isolated nucleic acid molecule comprising a DNA sequence selected from the group consisting of:
   a) SEQ ID NO: 8; and
   b) a DNA sequence that encodes an amino acid sequence as presented by SEQ ID NO: 7; and
   c) a DNA sequence that is degenerate as a result of the genetic code to the DNA sequence defined in (a) and which encodes an amino acid sequence as represented by SEQ ID NO: 7.

2. The isolated nucleic acid molecule according to claim 1, wherein the isolated nucleic acid molecule is represented by SEQ ID NO: 8.

3. A vector comprising the isolated nucleic acid molecule of claim 1.

4. The vector according to claim 3 wherein said isolated nucleic acid molecule is operably linked to a promoter.

5. The vector according to claim 4 wherein the promoter is an inducible promoter or a developmentally regulated promoter.

6. A cell transfected or transformed with at least one isolated nucleic acid molecule of claim 1.

7. The cell according to claim 6, wherein the at least one isolated nucleic acid molecule encodes a peptide having desaturase activity, and wherein the cell has at least part of a 3-n fatty acid biosynthetic pathway.

8. A cell transfected or transformed with the vector of claim 3.

9. The cell according to claim 6, wherein said cell is transfected or transformed with an nucleic acid molecule which comprises SEQ ID NO: 8.

10. The cell of claim 6, wherein the cell is a mammalian cell; a yeast cell; an algal cell; or a plant cell.

11. The cell according to claim 10, wherein the cell is a plant cell.

12. A plant comprising the cell according to claim 11.

13. The plant according to claim 12 wherein said plant is selected from the group consisting of: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolor, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Iopmoea batatus*), cassaya (*Manihot esculenta*), coffee (*Cofea* spp.), coconut (*Cocos nucifera*), pineapple (*Anana comosus*), citris tree (*Citrus* spp.) cocoa (*Theobroma cacao*), tea (*Camellia senensis*), banana (*Musa* spp.), avocado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

14. A seed comprising the cell according to claim 11.

15. The cell according to claim 10, wherein the yeast cell is a member of the genus *Saccharomyces* spp.

16. The cell according to claim 15, wherein said yeast cell is *Saccharomyces cerevisiae*.

17. A method of modulating a level of a fatty acid in a plant cell comprising;
   providing a plant cell according to claim 11;
   regenerating the plant cell into a plant; and
   monitoring fatty acid production by said plant.

18. A method for producing a fatty acid, comprising:
   providing the plant cell of claim 6; and
   providing conditions conducive to growth of said cell, wherein the cell thereby produces a fatty acid.

19. A method for producing a fatty acid, comprising:
   providing the plant cell of claim 11;
   regenerating said cell into a plant; and
   extracting fatty acids, or variants thereof, from said plant, thereby producing a fatty acid.

20. The method of claim 18, further comprising extracting fatty acids or variants thereof from the cell.

* * * * *

SEQUENCE LISTING

```
<160> NUMBER OF SEQ ID NOS: 19

<210> SEQ ID NO 1
<211> LENGTH: 1734
<212> TYPE: DNA
<213> ORGANISM: Pavlova lutherii

<400> SEQUENCE: 1
cacgaggcct cgtgccgaat tcggcacgag ggctgcgcga cgacaaggac gacggcagcc      60
tgagtgcgac gagcgatttc ttccgctcga cgatcacgga ttgcggcaat ttttgcgacg     120
agtcggtcga cttccagatg aagcttttg agcgcaacca gatctccgag cgctgctact     180
tcccacctgg catccgcgcc taccgcaagg gcgagcgcga cttttgacttt tcgatggccg     240 ccgcgcgcaa ggagttcgag actgtcgtct tcacgaccgt cgacgagctg ctcgccaaga     300
cgggcgtaaa gccgcgagat atcgacatcc tcgtcgtcaa ctgctcgctc ttcaacccga     360
```

```
cgccatcgct ggctgcgatc gtgatcaacc actaccagat gaaggactcc gtacagagct    420
actcacttgg cgggatgggt tgctcagcgg gactcatctc aatccacctc gcaaaggacc    480
tgctgcaggt ctacccgcgc aagcgcgcgc tcgtcatctc gacggagaac atcacgcaaa    540
attttacca gggcaacgaa aagtcgatgc tcatctcgaa cacgctcttc cgaatgggcg    600
gcgccgccgt cctcctctcc ggccgccacg ccgaccggcg cgtcgccaag tatcaactgc    660
tgcacaccgt ccgcacgcac aagggcgcgg acccggacgc gtaccggtgc gtcttccagg    720
aggaggacaa ggcggggcac gtgggcgtgc gcctgtcgaa agacgtgatg gagtgcgccg    780
gcgccgcgat gaagaccaac atctccgtcc tcgcgcctct gattctgccc gtttctgagc    840
aggtccgatt tctcgcaaac tacgttgcgc gcaagtggct gcgaatgaaa ggcgtgaagg    900
gatacgtgcc ggacttcaca acggccgtgc agcactttg catccacacg ggcgggcgcg    960
cggtgctcga cgcgctgcag gcgaacttgt cgctctcaga ttactacctc gagccgagcc    1020
gttactccct gtggcgctgg ggtaacgtct caagcgcctc agtctggtac gagctcgact    1080
ggctcgaaaa gtccggccgc atccggcggg cgacaaggt gtggcagatt gggtttggca    1140
gcggcttcaa gtgcaactcg gccgtctggc gggcgtgccg agcgatgccc tagctacgcc    1200
ggcgccgtcc gcattgccag tggttcgtga cagacagtca cactgacgag tgcggagtga    1260
cgtctgacgc cttccccccc ccgcccacca cctccacctc cacctccttc actctcactc    1320
aatcgcgcgg cggccagagc aggagcgcgc tcgtgctcgc catcaccgcc ttgtagtcct    1380
cgcgccgctc gagcgagcgc gcgtccatga gcggcacgga cgcgaagcgg aagaagagcc    1440
acatcacagc agaaaaaaaa aaaaaaaaaa actcgagact agttctctct accgcgctgc    1500
cgagctcaag cacggccgcg tgtgcatgct cgccgtcacc ggcatgcttg tccaggaggt    1560
gtactcgtgg ccggcacccg acggcgtctt caaggcgccg acgccgctcg gcgcgctctc    1620
gaccgtgccg gcgctcggcc tcatccagct catcgtcttc ctcggcatca tcgaggtgcg    1680
ctcggcgaac taccagggcc gcgtgcccgg cgaccttggc tttgacccgc tcgg          1734
```

<210> SEQ ID NO 2
<211> LENGTH: 396
<212> TYPE: PRT
<213> ORGANISM: Pavlova lutherii

<400> SEQUENCE: 2

```
Arg Gly Leu Val Pro Asn Ser Ala Arg Gly Leu Arg Asp Asp Lys Asp
1               5                   10                  15

Asp Gly Ser Leu Ser Ala Thr Ser Asp Phe Phe Arg Ser Thr Ile Thr
            20                  25                  30

Asp Cys Gly Asn Phe Cys Asp Glu Ser Val Asp Phe Gln Met Lys Leu
        35                  40                  45

Phe Glu Arg Asn Gln Ile Ser Glu Arg Cys Tyr Phe Pro Pro Gly Ile
    50                  55                  60

Arg Ala Tyr Arg Lys Gly Glu Arg Asp Phe Asp Phe Ser Met Ala Ala
65                  70                  75                  80

Ala Arg Lys Glu Phe Glu Thr Val Val Phe Thr Thr Val Asp Glu Leu
                85                  90                  95

Leu Ala Lys Thr Gly Val Lys Pro Arg Asp Ile Asp Ile Leu Val Val
            100                 105                 110

Asn Cys Ser Leu Phe Asn Pro Thr Pro Ser Leu Ala Ala Ile Val Ile
        115                 120                 125

Asn His Tyr Gln Met Lys Asp Ser Val Gln Ser Tyr Ser Leu Gly Gly
```

```
                    130                 135                 140
Met Gly Cys Ser Ala Gly Leu Ile Ser Ile His Leu Ala Lys Asp Leu
145                 150                 155                 160

Leu Gln Val Tyr Pro Arg Lys Arg Ala Leu Val Ile Ser Thr Glu Asn
                165                 170                 175

Ile Thr Gln Asn Phe Tyr Gln Gly Asn Glu Lys Ser Met Leu Ile Ser
                180                 185                 190

Asn Thr Leu Phe Arg Met Gly Gly Ala Ala Val Leu Leu Ser Gly Arg
                195                 200                 205

His Ala Asp Arg Arg Val Ala Lys Tyr Gln Leu Leu His Thr Val Arg
210                 215                 220

Thr His Lys Gly Ala Asp Pro Asp Ala Tyr Arg Cys Val Phe Gln Glu
225                 230                 235                 240

Glu Asp Lys Ala Gly His Val Gly Val Arg Leu Ser Lys Asp Val Met
                245                 250                 255

Glu Cys Ala Gly Ala Ala Met Lys Thr Asn Ile Ser Val Leu Ala Pro
                260                 265                 270

Leu Ile Leu Pro Val Ser Glu Gln Val Arg Phe Leu Ala Asn Tyr Val
                275                 280                 285

Ala Arg Lys Trp Leu Arg Met Lys Gly Val Lys Gly Tyr Val Pro Asp
                290                 295                 300

Phe Thr Thr Ala Val Gln His Phe Cys Ile His Thr Gly Gly Arg Ala
305                 310                 315                 320

Val Leu Asp Ala Leu Gln Ala Asn Leu Ser Leu Ser Asp Tyr Tyr Leu
                325                 330                 335

Glu Pro Ser Arg Tyr Ser Leu Trp Arg Trp Gly Asn Val Ser Ser Ala
                340                 345                 350

Ser Val Trp Tyr Glu Leu Asp Trp Leu Glu Lys Ser Gly Arg Ile Arg
                355                 360                 365

Arg Gly Asp Lys Val Trp Gln Ile Gly Phe Gly Ser Gly Phe Lys Cys
            370                 375                 380

Asn Ser Ala Val Trp Arg Ala Cys Arg Ala Met Pro
385                 390                 395

<210> SEQ ID NO 3
<211> LENGTH: 1113
<212> TYPE: DNA
<213> ORGANISM: Pavlova lutherii

<400> SEQUENCE: 3
gcacgaggcc tcgtgccgaa ttcggcacga ggcggcgctg tggtcgtggt taccgacgta      60
cgacgagttt gtcgatgggc tttcgttcgt cgaccgcgaa agatcggcg tgcacatggt     120
cgaccagggc gtgattacct ctgcggagtg ggcggccatc tcggtcgaca agcacatgtc     180
cttcttctcc gacgcggccg agttcacggg cgaccactgg atcatcccgc tcgtcgcggt     240
cgcactctac ctcgtgatga tcgtcgtcgg cccaatgatc atggccaacc ggccgccgct     300
ccccgtgaat gggctcgcct cgcgtggaa ctggttcctg ccgcattca gcactttcgg     360
cgtggcttgc acgtggcact gtatcttcac caggctgcgt agccgcggct cgagagcac     420
gacgtgcggc agcgccatgt tcatgtcgca ggggtacgtt ggcttggcaa tgctgctctt     480
catctactcc aagctcttcg agttgatcga caccttcttc ctcatcgcga agaaggcgga     540
tgtgatcttc ctgcattggt accaccacgt caccgtgctg ctctactgct ggcactcgca     600
ctcggtccgg ataccgagcg ggatctggtt cgccgcgatg aactactttg tgcacgccat     660
```

```
catgtactcc tactttgcga tgacgcagat gggtccgcgc taccgcaagc tcgtccggcc      720
gtacgcgcgg ctgattacga ccctgcagat ctcgcagatg ttcgtcggcc tcatcgtcaa      780
cggctcgatc atttacttca cgtcgctcgg gcacgcatgc aagtcgagca agacgaacac      840
gatcctgagc tggctgatgt acctcagcta ctttgtgcta ttcggactgc tctacctgcg      900
caattacatc cttggtacac atggcaagcc ggcgggcaag cgcgcaaagg caaggcgga      960 atagtgcagg ggccggggag gcggtgccca cccgcgctcg caaagcggtc gcgctccttg     1020
ccgagatgcg acgagagtcg aagaggtgaa acctccttaa aataatgcta ctcctagatt     1080
ttcgctttgt gcttccgtat agatggtcaa gcc                                  1113
```

<210> SEQ ID NO 4
<211> LENGTH: 320
<212> TYPE: PRT
<213> ORGANISM: Pavlova lutherii

<400> SEQUENCE: 4

```
His Glu Ala Ser Cys Arg Ile Arg His Glu Ala Ala Leu Trp Ser Trp
1               5                   10                  15

Leu Pro Thr Tyr Asp Glu Phe Val Asp Gly Leu Ser Phe Val Asp Arg
            20                  25                  30

Glu Lys Ile Gly Val His Met Val Asp Gln Gly Val Ile Thr Ser Ala
        35                  40                  45

Glu Trp Ala Ala Ile Ser Val Asp Lys His Met Ser Phe Phe Ser Asp
    50                  55                  60

Ala Ala Glu Phe Thr Gly Asp His Trp Ile Ile Pro Leu Val Ala Val
65                  70                  75                  80

Ala Leu Tyr Leu Val Met Ile Val Val Gly Pro Met Ile Met Ala Asn
                85                  90                  95

Arg Pro Pro Leu Pro Val Asn Gly Leu Ala Cys Ala Trp Asn Trp Phe
            100                 105                 110

Leu Ala Ala Phe Ser Thr Phe Gly Val Ala Cys Thr Trp His Cys Ile
        115                 120                 125

Phe Thr Arg Leu Arg Ser Arg Gly Phe Glu Ser Thr Thr Cys Gly Ser
    130                 135                 140

Ala Met Phe Met Ser Gln Gly Tyr Val Gly Leu Ala Met Leu Leu Phe
145                 150                 155                 160

Ile Tyr Ser Lys Leu Phe Glu Leu Ile Asp Thr Phe Phe Leu Ile Ala
                165                 170                 175

Lys Lys Ala Asp Val Ile Phe Leu His Trp Tyr His Val Thr Val
            180                 185                 190

Leu Leu Tyr Cys Trp His Ser His Ser Val Arg Ile Pro Ser Gly Ile
        195                 200                 205

Trp Phe Ala Ala Met Asn Tyr Phe Val His Ala Ile Met Tyr Ser Tyr
    210                 215                 220

Phe Ala Met Thr Gln Met Gly Pro Arg Tyr Arg Lys Leu Val Arg Pro
225                 230                 235                 240

Tyr Ala Arg Leu Ile Thr Thr Leu Gln Ile Ser Gln Met Phe Val Gly
                245                 250                 255

Leu Ile Val Asn Gly Ser Ile Ile Tyr Phe Ser Leu Gly His Ala
            260                 265                 270

Cys Lys Ser Ser Lys Thr Asn Thr Ile Leu Ser Trp Leu Met Tyr Leu
        275                 280                 285
```

```
Ser Tyr Phe Val Leu Phe Gly Leu Leu Tyr Leu Arg Asn Tyr Ile Leu
    290                 295                 300

Gly Thr His Gly Lys Pro Ala Gly Lys Arg Ala Lys Gly Lys Ala Glu
305                 310                 315                 320
```

<210> SEQ ID NO 5
<211> LENGTH: 480
<212> TYPE: DNA
<213> ORGANISM: Pavlova lutherii

<400> SEQUENCE: 5

```
cacgaggcga atgtgggcgg ctactggctt ggcgtgctca atggagggct caacttccag      60
atcgagcacc atcttttccc gcggctgcac cattcgtact acgcgcagat tgccccagtg     120
gtgcgcacgc acatcgagaa gctcggcttc aagtacaggc acttcccac ggtgggctcc     180
aacttgtcgt ccatgctgca gcacatgggc aagatgggca ctcgcccagg agctgagaag     240
ggcggcaagg ccgagtgagc tgccgcccta ccctgcctct gcggctagcc agcaaccggg     300
tgccagcgag cccctcttcc atccgagccc ttttctcctt caccctgcca tgtgtcagcg     360
gcactgactg aactgacgtc gccgtgccgc tggcgctctc cgtcgccagc cactgagagg     420
ctgcaatgcc gcccgacgcc gctcacgcgg ctttggtctt aaaaaaaaaa aaaaaaaaaa     480
```

<210> SEQ ID NO 6
<211> LENGTH: 85
<212> TYPE: PRT
<213> ORGANISM: Pavlova lutherii

<400> SEQUENCE: 6

```
His Glu Ala Asn Val Gly Gly Tyr Trp Leu Gly Val Leu Asn Gly Gly
1               5                   10                  15

Leu Asn Phe Gln Ile Glu His His Leu Phe Pro Arg Leu His His Ser
            20                  25                  30

Tyr Tyr Ala Gln Ile Ala Pro Val Val Arg Thr His Ile Glu Lys Leu
        35                  40                  45

Gly Phe Lys Tyr Arg His Phe Pro Thr Val Gly Ser Asn Leu Ser Ser
    50                  55                  60

Met Leu Gln His Met Gly Lys Met Gly Thr Arg Pro Gly Ala Glu Lys
65                  70                  75                  80

Gly Gly Lys Ala Glu
            85
```

<210> SEQ ID NO 7
<211> LENGTH: 445
<212> TYPE: PRT
<213> ORGANISM: Pavlova lutherii

<400> SEQUENCE: 7

```
Met Pro Pro Ser Ala Ala Ser Glu Gly Gly Val Ala Glu Leu Arg Ala
1               5                   10                  15

Ala Glu Val Ala Ser Tyr Thr Arg Lys Ala Val Asp Glu Arg Pro Asp
            20                  25                  30

Leu Thr Ile Val Gly Asp Ala Val Tyr Asp Ala Lys Ala Phe Arg Asp
        35                  40                  45

Glu His Pro Val Gly Ala His Phe Val Ser Leu Phe Gly Gly Arg Asp
    50                  55                  60

Ala Thr Glu Ala Phe Met Glu Tyr His Arg Arg Thr Trp Pro Lys Ala
65                  70                  75                  80
```

```
Arg Met Ser Lys Phe Phe Val Gly Ser Leu Asp Ala Ser Glu Lys Pro
                 85                  90                  95

Thr Gln Ala Asp Ser Ala Tyr Leu Arg Leu Cys Ala Glu Val Asn Ala
            100                 105                 110

Leu Leu Pro Lys Gly Ser Gly Phe Ala Pro Ser Tyr Trp Leu
        115                 120                 125

Lys Ala Ala Ala Leu Val Val Ala Ala Val Ser Ile Glu Gly Tyr Met
130                 135                 140

Leu Leu Arg Gly Lys Thr Leu Leu Leu Ser Val Phe Leu Gly Leu Val
145                 150                 155                 160

Phe Ala Trp Ile Gly Leu Asn Ile Gln His Asp Ala Asn His Gly Ala
                165                 170                 175

Leu Ser Arg His Ser Val Ile Asn Tyr Cys Leu Gly Tyr Ala Gln Asp
            180                 185                 190

Trp Ile Gly Gly Asn Met Val Leu Trp Leu Gln Glu His Val Val Met
        195                 200                 205

His His Leu His Thr Asn Asp Val Asp Ala Asp Pro Asp Gln Lys Ala
210                 215                 220

His Gly Val Leu Arg Leu Lys Pro Thr Asp Gly Trp Met Pro Trp His
225                 230                 235                 240

Ala Leu Gln Gln Leu Tyr Ile Leu Pro Gly Glu Ala Met Tyr Ala Phe
                245                 250                 255

Lys Leu Leu Phe Leu Asp Ala Leu Glu Leu Leu Ala Trp Arg Trp Glu
            260                 265                 270

Gly Glu Lys Ile Ser Pro Leu Ala Arg Ala Leu Phe Ala Pro Ala Val
        275                 280                 285

Ala Cys Lys Leu Gly Phe Trp Ala Arg Phe Val Ala Leu Pro Leu Trp
290                 295                 300

Leu Gln Pro Thr Val His Thr Ala Leu Cys Ile Cys Ala Thr Val Cys
305                 310                 315                 320

Thr Gly Ser Phe Tyr Leu Ala Phe Phe Phe Ile Ser His Asn Phe
                325                 330                 335

Asp Gly Val Gly Ser Val Gly Pro Lys Gly Ser Leu Pro Arg Ser Ala
            340                 345                 350

Thr Phe Val Gln Arg Gln Val Glu Thr Ser Ser Asn Val Gly Gly Tyr
        355                 360                 365

Trp Leu Gly Val Leu Asn Gly Leu Asn Phe Gln Ile Glu His His
370                 375                 380

Leu Phe Pro Arg Leu His His Ser Tyr Tyr Ala Gln Ile Ala Pro Val
385                 390                 395                 400

Val Arg Thr His Ile Glu Lys Leu Gly Phe Lys Tyr Arg His Phe Pro
                405                 410                 415

Thr Val Gly Ser Asn Leu Ser Ser Met Leu Gln His Met Gly Lys Met
            420                 425                 430

Gly Thr Arg Pro Gly Ala Glu Lys Gly Gly Lys Ala Glu
        435                 440                 445

<210> SEQ ID NO 8
<211> LENGTH: 1619
<212> TYPE: DNA
<213> ORGANISM: Pavlova lutherii

<400> SEQUENCE: 8
acgcggtgtc acgcgcgtct tccagcgcga gccgctgctc cgccgcgaag tctctaggca      60
```

-continued

```
tgccgccttc ggccgcgagc gagggcggcg tggcggagct gcgcgcgcg gaggtcgcct      120
cgtacacgcg caaggcggtg gatgagcgcc ccgacctcac catcgtcggc gatgccgtct      180
acgacgccaa ggccttccgt gacgagcacc cggtcggcgc ccactttgtg agcctctttg      240
gcgggcgcga cgcgaccgag gcgttcatgg agtaccaccg gcggacgtgg cccaaggcgc      300
ggatgagcaa gttcttcgtg ggctcgctca cgcctccga gaagccgacg caggccgaca      360
gtgcctacct ccggctgtgc gcggaggtga acgccttgct gccaaagggg agcggcggct      420
ttgcgccgcc ctcctattgg ctcaaggcgg cggcgctggt ggtggccgcc gtgtcgattg      480
aggggtatat gctgctgcgc ggcaagacgc tcctcctctc cgtctttctc ggcctcgtct      540
ttgcgtggat cggtctcaac atccagcacg acgcgaacca cggcgcgctc tcgcgccact      600
cggtgatcaa ctactgcctt gggtacgcgc aggactggat cggcggcaac atggcgctct      660
ggctgcagga gcacgtggtg atgcaccacc tgcacaccaa cgacgtcgac gccgacccgg      720
accagaaggc gcacgcgtg ctgcggctca gccaacgga cggctggatg ccgtggcatg      780
cgctccaaca gctttacatt ctgcccggcg aggcgatgta cgcgtttaag ctgctcttcc      840
tcgacgcgct cgagctgctc gcgtggcgat gggaggcga aagatctcg ccctcgcgc      900
gcgccctgtt tgcaccagcg gtggcgtgca agcttggctt ctgggcgcgc ttcgtcgcgc      960
tgccgctctg gctgcagccg acggtgcaca cggcgctgtg catctgcgcg acggtgtgca     1020
cgggctcctt ctacctcgcc ttcttcttct tcatctcgca caactttgac ggcgtgggta     1080
gtgtgggccc caagggcagc ttgccgcgct ctgcaacctt cgtgcagcgg caggtcgaga     1140
cgagttcgaa tgtgggcggc tactggcttg gcgtgctcaa tggagggctc aacttccaga     1200
tcgagcacca tcttttcccg cggctgcacc attcgtacta cgcgcagatt gccccagtgg     1260
tgcgcacgca catcgagaag ctcggcttca agtacaggca cttccccacg gtgggctcca     1320
acttgtcgtc catgctgcag cacatgggca agatgggcac tcgcccagga gctgagaagg     1380
gcggcaaggc cgagtgagct gccgccctac cctgcctctg cggctagcca gcaaccgggt     1440
gccagcgagc ccctcttcca tccgagccct tttctcctcc accctgccat gtgtcagcgg     1500
cactgactga actgacgtcg ccgtgccgct ggcgctctcc gtcgccagcc actgagaggc     1560
tgcaatgccg cccgacgccg ctcacgcggc tttggtctta aaaaaaaaaa aaaaaaaa       1619
```

<210> SEQ ID NO 9
<211> LENGTH: 682
<212> TYPE: DNA
<213> ORGANISM: Pavlova lutherii

<400> SEQUENCE: 9

```
gcacgagggt gctgctacct gctgtacgtc tccctcggct cgatgtacat cttctgcaac       60
tttgccgtgt cgcacacgca cctgcccatc gttgaggccg accagcacgc cacctgggtt      120
gagtactcgg ccaaccacac gaccaactgc gcgccctcgt ggtggtgcga ctggtggatg      180
tcttacctca actaccagat cgagcatcat ctgttcccgt ccatgccgca attccgccac      240
ccgacgatcg cgccgcgcgt caaggcgctc ttcgagaagc acgggctgca ctatgacgtg      300
cgcggctact ttgaggcgat ggccgacacg ttcatgaacc ttgacaaggt cggcaacgcg      360
cacgagcaca accattaggc cgtagccgct tggaaagagg cctcctgcat acgcggcgac      420
gcgtcggcgc gcggcggcgt gcacgggagc acaaagtgat ggatggacct tgggcgacgc      480
cgacggccaa ggagtggttg tctctgtcgt cgccagggcc caggagccca ggggcagggt      540
tgcagagctt gggcgcgatt ggaggcaggg ccgggcgcgt cggcgttcgc gagtctggcg      600
```

```
aggcgctctg cgagctctgc acgactgcgc ccagaggcgt gcgcgcgcgc gcgagttcca    660
aaaaaaaaaa aaaaaaaaaa aa                                             682
```

<210> SEQ ID NO 10
<211> LENGTH: 125
<212> TYPE: PRT
<213> ORGANISM: Pavlova lutherii

<400> SEQUENCE: 10

```
Ala Arg Gly Cys Cys Tyr Leu Leu Tyr Val Ser Leu Gly Ser Met Tyr
1               5                   10                  15

Ile Phe Cys Asn Phe Ala Val Ser His Thr His Leu Pro Ile Val Glu
            20                  25                  30

Ala Asp Gln His Ala Thr Trp Val Glu Tyr Ser Ala Asn His Thr Thr
        35                  40                  45

Asn Cys Ala Pro Ser Trp Trp Cys Asp Trp Trp Met Ser Tyr Leu Asn
    50                  55                  60

Tyr Gln Ile Glu His His Leu Phe Pro Ser Met Pro Gln Phe Arg His
65                  70                  75                  80

Pro Thr Ile Ala Pro Arg Val Lys Ala Leu Phe Glu Lys His Gly Leu
                85                  90                  95

His Tyr Asp Val Arg Gly Tyr Phe Glu Ala Met Ala Thr Phe Met
            100                 105                 110

Asn Leu Asp Lys Val Gly Asn Ala His Glu His Asn His
        115                 120                 125
```

<210> SEQ ID NO 11
<211> LENGTH: 519
<212> TYPE: PRT
<213> ORGANISM: Thraustochytrium aureum

<400> SEQUENCE: 11

```
Met Thr Val Gly Tyr Asp Glu Glu Ile Pro Phe Glu Gln Val Arg Ala
1               5                   10                  15

His Asn Lys Pro Asp Asp Ala Trp Cys Ala Ile His Gly His Val Tyr
            20                  25                  30

Asp Val Thr Lys Phe Ala Ser Val His Pro Gly Gly Asp Ile Ile Leu
        35                  40                  45

Leu Ala Gly Lys Glu Ala Thr Val Leu Tyr Glu Thr Tyr His Val Arg
    50                  55                  60

Gly Val Ser Asp Ala Val Leu Arg Lys Tyr Arg Ile Gly Lys Leu Pro
65                  70                  75                  80

Asp Gly Gln Gly Gly Ala Asn Glu Lys Glu Lys Arg Thr Leu Ser Gly
                85                  90                  95

Leu Ser Ser Ala Ser Tyr Tyr Thr Trp Asn Ser Asp Phe Tyr Arg Val
            100                 105                 110

Met Arg Glu Arg Val Val Ala Arg Leu Lys Glu Arg Gly Lys Ala Arg
        115                 120                 125

Arg Gly Gly Tyr Glu Leu Trp Ile Lys Ala Phe Leu Leu Val Gly
    130                 135                 140

Phe Trp Ser Ser Leu Tyr Trp Met Cys Thr Leu Asp Pro Ser Phe Gly
145                 150                 155                 160

Ala Ile Leu Ala Ala Met Ser Leu Gly Val Phe Ala Ala Phe Val Gly
                165                 170                 175

Thr Cys Ile Gln His Asp Gly Asn His Gly Ala Phe Ala Gln Ser Arg
```

```
                    180                 185                 190
Trp Val Asn Lys Val Ala Gly Trp Thr Leu Asp Met Ile Gly Ala Ser
            195                 200                 205

Gly Met Thr Trp Glu Phe Gln His Val Leu Gly His His Pro Tyr Thr
        210                 215                 220

Asn Leu Ile Glu Glu Asn Gly Leu Gln Lys Val Ser Gly Lys Lys
225                 230                 235                 240

Met Asp Thr Lys Leu Ala Asp Gln Glu Ser Asp Pro Asp Val Phe Ser
                245                 250                 255

Thr Tyr Pro Met Met Arg Leu His Pro Trp His Gln Lys Arg Trp Tyr
            260                 265                 270

His Arg Phe Gln His Ile Tyr Gly Pro Phe Ile Phe Gly Phe Met Thr
        275                 280                 285

Ile Asn Lys Val Val Thr Gln Asp Val Gly Val Val Leu Arg Lys Arg
290                 295                 300

Leu Phe Gln Ile Asp Ala Glu Cys Arg Tyr Ala Ser Pro Met Tyr Val
305                 310                 315                 320

Ala Arg Phe Trp Ile Met Lys Ala Leu Thr Val Leu Tyr Met Val Ala
                325                 330                 335

Leu Pro Cys Tyr Met Gln Gly Pro Trp His Gly Leu Lys Leu Phe Ala
            340                 345                 350

Ile Ala His Phe Thr Cys Gly Glu Val Leu Ala Thr Met Phe Ile Val
        355                 360                 365

Asn His Ile Ile Glu Gly Val Ser Tyr Ala Ser Lys Asp Ala Val Lys
370                 375                 380

Gly Thr Met Ala Pro Pro Lys Thr Met His Gly Val Thr Pro Met Asn
385                 390                 395                 400

Asn Thr Arg Lys Glu Val Glu Ala Glu Ala Ser Lys Ser Gly Ala Val
                405                 410                 415

Val Lys Ser Val Pro Leu Asp Asp Gly Trp Ala Val Val Gln Cys Gln
            420                 425                 430

Thr Ser Val Asn Trp Ser Val Gly Ser Trp Phe Trp Asn His Phe Ser
        435                 440                 445

Gly Gly Leu Asn His Gln Ile Glu His His Leu Phe Pro Gly Leu Ser
450                 455                 460

His Glu Thr Tyr Tyr His Ile Gln Asp Val Phe Gln Ser Thr Cys Ala
465                 470                 475                 480

Glu Tyr Gly Val Pro Tyr Gln His Glu Pro Ser Ile Trp Thr Ala Tyr
                485                 490                 495

Trp Lys Met Leu Glu His Leu Arg Gln Leu Gly Asn Glu Glu Thr His
            500                 505                 510

Glu Ser Trp Gln Arg Ala Ala
        515

<210> SEQ ID NO 12
<211> LENGTH: 1340
<212> TYPE: DNA
<213> ORGANISM: Pavlova lutherii

<400> SEQUENCE: 12
gcacgaggcc tcttcggctg ggcgctcgac gacgcgctcg ccaagtatga caagggcggc      60
gtcggccccg gcttcctgta caacgcggtc gtcttctcgt cggtgcaggc gctgctcggc     120
ggtcgcgtgc gcatgatggt cgccggctcc gcgcccctct ccgccgacgt gcagaagttt     180
```

-continued

```
gtgcaatcgt gcttcaacgc gccgcttcgc caaggctacg gcctcaccga gacgtgcgcg        240
gcgacgacgc tctgcgcgct gcacgacaac acgccgtcgc aagttgggcc gccgcaggag        300
tcggcgtgca tcacgctgcg cgactgggag gagggcaact accgcaaccg cgacgccaac        360
gacccggcca tcgggatgcg cgcggcgag atcctgatcg gtgggcccgc cgtctgcctc         420
ggctactacg tgaacgagcg cgcgcccgac gcggacgtgg tgaagcgcaa cgcggaggac        480
tttgtgacga tcaacggcat gcgcttcttc tgctcgggcg acatcggcca gatcacgccg        540
agcggctgcg tgcagattat cgaccggaag aaggacctcg tcaagctgca gcagggcgag        600
tacgtcgcgc tctccaaggt ggagaacgcg ctcaagaact cgtcgtacac gcagatcccg        660
tacgtctacg cgctctcatc caagagctac tgcatcgcgc tcctctgccc gcagcacgcg        720
gcgatccgcc agctcgccgc ctcgctgcag atcagcggca aggagctttc cgagctgtgc        780
gcgcacccgc agatcgtcgc ggccgtgctc aaggacctgc aggcgcagtg caaggcggcc        840
aagctcgcgg gcttcgagac gccgagcaag ctcatcctcg tgtcggacga gtggaccgtt        900
gagaatgaca tgctcaccac gacgatgaag atcaagcgca agccaatcgc tgaccggcac        960
gcgagcgaga tcaaggccgt ttacgtctga gcccgcgcct ttttgtacaa cctcgagagc       1020
gccactgtct tgatggcgcg cgcgtgctgt tgtgcaggcc gtcggcattg accgcggcgc       1080
ttgaacgcaa ggcaggcgca aggcgcggga gggattgctg gggatggcgg ctgccgcagt       1140
tgctgagcag aaggcagtct ccggctctcg acaggtggcg cccgttgtgc agaatgttcg       1200
cagcccctcc ccctcgggc ggctgccatt cggggcagcg ctcgcacatg tgctgcgctc       1260
cgcagccgca cgccacggcc accaacgcgt gtgcctgccg tcacgcgccg cgcccgtggg       1320
aacgaccgtt gccctcgcac                                                   1340
```

<210> SEQ ID NO 13
<211> LENGTH: 329
<212> TYPE: PRT
<213> ORGANISM: Pavlova lutherii

<400> SEQUENCE: 13

```
Ala Arg Gly Leu Phe Gly Trp Ala Leu Asp Asp Ala Leu Ala Lys Tyr
1               5                   10                  15

Asp Lys Gly Gly Val Gly Pro Gly Phe Leu Tyr Asn Ala Val Val Phe
            20                  25                  30

Ser Ser Val Gln Ala Leu Leu Gly Gly Arg Val Arg Met Met Val Ala
        35                  40                  45

Gly Ser Ala Pro Leu Ser Ala Asp Val Gln Lys Phe Val Gln Ser Cys
    50                  55                  60

Phe Asn Ala Pro Leu Arg Gln Gly Tyr Gly Leu Thr Glu Thr Cys Ala
65                  70                  75                  80

Ala Thr Thr Leu Cys Ala Leu His Asp Asn Thr Pro Ser Gln Val Gly
                85                  90                  95

Pro Pro Gln Glu Ser Ala Cys Ile Thr Leu Arg Asp Trp Glu Glu Gly
            100                 105                 110

Asn Tyr Arg Asn Arg Asp Ala Asn Asp Pro Ala Ile Gly Met Arg Arg
        115                 120                 125

Gly Glu Ile Leu Ile Gly Gly Pro Ala Val Cys Leu Gly Tyr Tyr Val
    130                 135                 140

Asn Glu Arg Ala Pro Asp Ala Asp Val Val Lys Arg Asn Ala Glu Asp
145                 150                 155                 160

Phe Val Thr Ile Asn Gly Met Arg Phe Phe Cys Ser Gly Asp Ile Gly
```

-continued

```
                      165                 170                 175
Gln Ile Thr Pro Ser Gly Cys Val Gln Ile Ile Asp Arg Lys Lys Asp
            180                 185                 190
Leu Val Lys Leu Gln Gln Gly Glu Tyr Val Ala Leu Ser Lys Val Glu
            195                 200                 205
Asn Ala Leu Lys Asn Ser Ser Tyr Thr Gln Ile Pro Tyr Val Tyr Ala
            210                 215                 220
Leu Ser Ser Lys Ser Tyr Cys Ile Ala Leu Leu Cys Pro Gln His Ala
225                 230                 235                 240
Ala Ile Arg Gln Leu Ala Ala Ser Leu Gln Ile Ser Gly Lys Glu Leu
                245                 250                 255
Ser Glu Leu Cys Ala His Pro Gln Ile Val Ala Ala Val Leu Lys Asp
            260                 265                 270
Leu Gln Ala Gln Cys Lys Ala Ala Lys Leu Ala Gly Phe Glu Thr Pro
            275                 280                 285
Ser Lys Leu Ile Leu Val Ser Asp Glu Trp Thr Val Glu Asn Asp Met
            290                 295                 300
Leu Thr Thr Thr Met Lys Ile Lys Arg Lys Pro Ile Ala Asp Arg His
305                 310                 315                 320
Ala Ser Glu Ile Lys Ala Val Tyr Val
                325

<210> SEQ ID NO 14
<211> LENGTH: 732
<212> TYPE: DNA
<213> ORGANISM: Pavlova lutherii

<400> SEQUENCE: 14
gcacgagggc tcgacctact gcccgcgctg cgcggcaaga tgcgctggct cgcggcgagc      60
gtgctctttc ggcttcccat cgtgcgcgag ctcacccttt ggaccggctg catcgacgcg     120
cgccgctcgg ttgccgagag tgcgctgcgt ggcggctact cagtcggcgt actgcccggc     180
ggcgagcagg agcagctgcg cacgcgctac gggcgcgagt cggtatattt cgcgaagcgc     240
tttggcttcg tcaagcttgc gctccgcttc ggcgtgccgc tcgtgcctgg gtacgtgttc     300
gggtgcgtcg acctgtacca cacttcatcc ctgctcttct cggcgcgcga gtggctcgtg     360
cgctctctcg gcgtgtgcgt gcccgtgtgc ttcggagcgt ggggcgtgcc catggcgccg     420
cttgctgtgc cgctcaacgt cgtgatcggc cggccgatca agctgccgcg caaccctgag     480
ccgaccgatg aggacgtcgc gcgcgcgctc gaccagtaca tcgccgcgct cgcgcgctc      540 tttgacgaga acaaggcgcg cttttggctat gccgaccgcg agctggaggt gtgctgattg     600
tgaagaagtg tcattgaagg tcggcgtcag caggcgcacc gcgcaccaag ccactcacgt     660
cttgatcgct gaaccgccgt gaacgatgcc gttgcgacac gcttgaagat ggccagaaaa     720
aaaaaaaaaa aa                                                         732

<210> SEQ ID NO 15
<211> LENGTH: 1099
<212> TYPE: DNA
<213> ORGANISM: Pavlova lutherii

<400> SEQUENCE: 15
actgcgtgta cacagcatgg cggctcgcgc ggttgacgcg ctcgtcgtga gcgcgttcac      60
ggcgttcgtg cagatcggcg tgtgggcgct cacgcccgtg ggcattgcgt gggccctcgc     120
gttccactgg aaggtgacgc tgccgctgct cgcccttttat ctcgcgtcgt acctcgacgg    180
```

```
cgccgaggtg cgcgtcaagc gcgtgcgcgc gtggccggcg ttctcccggc attttttggct    240 gttcacgttc atgcgcaggg tctaccggca gcgcgttcac gtgccagctg gcctcgaggc    300
cgaggagcag atcatcctag cgctgcatcc gcacggctcg atggcggact accgcgcgat    360
cctcgacggc cagctgctcg acctactgcc cgcgctgcgc ggcaagatgc gctggctcgc    420
ggcgagcgtg ctctttcggc ttcccatcgt gcgcgagctc accctttgga ccggctgcat    480
cgacgcgcgc cgctcggttg ccgagagtgc gctgcgtggc ggctactcag tcggcgtact    540
gcccggcggc gagcaggagc agctgcgcac gcgctacggg cgcgagtcgg tatatttgcg    600
caagcgcttt ggcttcgtca agcttgcgct ccgcttcggc gtgccgctcg tgcctgggta    660
cgtgttcggg tgcgtcgacc tgtaccacac ttcatccctg ctcttctcgg cgcgcgagtg    720
gctcgtgcgc tctctcggcg tgtgcgtgcc cgtgtgcttc ggagcgtggg gcgtgcccat    780
ggcgccgctt gctgtgccgc tcaacgtcgt gatcggccgg ccgatcaagc tgccgcgcaa    840
ccctgagccg accgatgagg acgtcgcgcg cgcgctcgac cagtacatcg ccgcgctgcg    900
cgcgctcttt gacgagaaca aggcgcgctt tggctatgcc gaccgcgagc tggaggtgtg    960
ctgattgtga agaagtgtca ttgaaggtcg gcgtcagcag gcgcaccgcg caccaagcca   1020
ctcacgtctt gatcgctgaa ccgccgtgaa cgatgccgtt gcgacacgct tgaagatggc   1080
cagaaaaaaa aaaaaaaaa                                                  1099
```

<210> SEQ ID NO 16
<211> LENGTH: 315
<212> TYPE: PRT
<213> ORGANISM: Pavlova lutherii

<400> SEQUENCE: 16

```
Met Ala Ala Arg Ala Val Asp Ala Leu Val Val Ser Ala Phe Thr Ala
1               5                   10                  15

Phe Val Gln Ile Gly Val Trp Ala Leu Thr Pro Val Gly Ile Ala Trp
            20                  25                  30

Ala Leu Ala Phe His Trp Lys Val Thr Leu Pro Leu Leu Ala Leu Tyr
        35                  40                  45

Leu Ala Ser Tyr Leu Asp Gly Ala Glu Val Arg Val Lys Arg Val Arg
    50                  55                  60

Ala Trp Pro Ala Phe Ser Arg His Phe Trp Leu Phe Thr Phe Met Arg
65                  70                  75                  80

Arg Val Tyr Arg Gln Arg Val His Val Pro Ala Gly Leu Glu Ala Glu
                85                  90                  95

Glu Gln Ile Ile Leu Ala Leu His Pro His Gly Ser Met Ala Asp Tyr
            100                 105                 110

Arg Ala Ile Leu Asp Gly Gln Leu Leu Asp Leu Leu Pro Ala Leu Arg
        115                 120                 125

Gly Lys Met Arg Trp Leu Ala Ala Ser Val Leu Phe Arg Leu Pro Ile
    130                 135                 140

Val Arg Glu Leu Thr Leu Trp Thr Gly Cys Ile Asp Ala Arg Arg Ser
145                 150                 155                 160

Val Ala Glu Ser Ala Leu Arg Gly Gly Tyr Ser Val Gly Val Leu Pro
                165                 170                 175

Gly Gly Glu Gln Glu Gln Leu Arg Thr Arg Tyr Gly Arg Glu Ser Val
            180                 185                 190

Tyr Leu Arg Lys Arg Phe Gly Phe Val Lys Leu Ala Leu Arg Phe Gly
        195                 200                 205
```

```
Val Pro Leu Val Pro Gly Tyr Val Phe Gly Cys Val Asp Leu Tyr His
    210                 215                 220

Thr Ser Ser Leu Leu Phe Ser Ala Arg Glu Trp Leu Val Arg Ser Leu
225                 230                 235                 240

Gly Val Cys Val Pro Val Cys Phe Gly Ala Trp Gly Val Pro Met Ala
                245                 250                 255

Pro Leu Ala Val Pro Leu Asn Val Val Ile Gly Arg Pro Ile Lys Leu
                260                 265                 270

Pro Arg Asn Pro Glu Pro Thr Asp Glu Asp Val Ala Arg Ala Leu Asp
            275                 280                 285

Gln Tyr Ile Ala Ala Leu Arg Ala Leu Phe Asp Glu Asn Lys Ala Arg
    290                 295                 300

Phe Gly Tyr Ala Asp Arg Glu Leu Glu Val Cys
305                 310                 315

<210> SEQ ID NO 17
<211> LENGTH: 2061
<212> TYPE: DNA
<213> ORGANISM: Pavlova lutherii

<400> SEQUENCE: 17
ggcacgaggg ggagatggcg gcgccgacat cgccgtacgg cgcggaatcg ccgcgcgcgg    60
cgtacgcgta cccggagcgt gcaaatgtca agatgtccga ggcgctgcgc gtactcgacg   120
agggcgtgca cccgctcgtt attcacagct cgcagatcct cgccgccgcg ctgctcgtca   180
cggccgccgt caaccacttt cccaagatca ccgtcgcgga cctcgccgag atctggcgct   240
cgctgcagat cgacgtggcg tacgcgttcg cgctgactgc ggtggccgtg ctgcttctcg   300
gctactacgc tctccgccac ccgcgccccg tctacctcgt cgacttcgcc acgtggcagc   360
tgcgcgacga caaggacgac ggcagcctga gtgcgacgag cgatttcttc cgctcgacga   420
tcacggattg cggcaatttt tgcgacgagt cggtcgactt ccagatgaag cttttgagc    480 gcaaccagat ctccgagcgc tgctacttcc cacctggcat ccgcgcctac cgcaagggcg   540
agcgcgactt tgacttttcg atggccgccg cgcgcaagga gttcgagact gtcgtcttca   600
cgaccgtcga cgagctgctc gccaagacgg gcgtaaagcc gcgagatatc gacatcctcg   660
tcgtcaactg ctcgctcttc aacccgacgc catcgctggc tgcgatcgtg atcaaccact   720
accagatgaa ggactccgta cagagctact cacttggcgg gatgggttgc tcagcgggac   780
tcatctcaat ccacctcgca aaggacctgc tgcaggtcta cccgcgcaag cgcgcgctcg   840
tcatctcgac ggagaacatc acgcaaaatt tttaccaggg caacgaaaag tcgatgctca   900
tctcgaacac gctcttccga atgggcggcg ccgccgtcct cctctccggc cgccacgccg   960
accggcgcgt cgccaagtat caactgctgc acaccgtccg cacgcacaag ggcgcggacc  1020
cggacgcgta ccggtgcgtc ttccaggagg aggacaaggc ggggcacgtg ggcgtgcgcc  1080
tgtcgaaaga cgtgatggag tgcgccggcg ccgcgatgaa gaccaacatc tccgtcctcg  1140
cgcctctgat tctgcccgtt tctgagcagg tccgatttct cgcaaactac gttgcgcgca  1200
agtggctgcg aatgaaaggc gtgaagggat acgtgccgga cttcacaacg gccgtgcagc  1260
acttttgcat ccacacgggc gggcgcgcgg tgctcgacgc gctgcaggcg aacttgtcgc  1320
tctcagatta ctacctcgag ccgagccgtt actccctgtg cgctggggt aacgtctcaa  1380 gcgcctcagt ctggtacgag ctcgactggc tcgaaaagtc cggccgcatc cggcggggcg  1440
acaaggtgtg gcagattggg tttggcagcg gcttcaagtg caactcggcc gtctggcggg  1500
```

-continued

```
cgtgccgagc gatgccctag ctacgccggc gccgtccgca ttgccagtgg ttcgtgacag    1560
acagtcacac tgacgagtgc ggagtgacgt ctgacgcctt ccccccccg cccaccacct    1620 ccacctccac ctccttcact ctcactcaat cgcgcggcgg ccagagcagg agcgcgctcg    1680
tgctcgccat caccgccttg tagtcctcgc gccgctcgag cgagcgcgcg tccatgagcg    1740
gcacggacgc gaagcggaag aagagccaca tcacagcaga aaaaaaaaaa aaaaaaaact    1800
cgagactagt tctctctacc gcgctgccga gctcaagcac ggccgcgtgt gcatgctcgc    1860
cgtcaccggc atgcttgtcc aggaggtgta ctcgtggccg gcacccgacg gcgtcttcaa    1920
ggcgccgacg ccgctcggcg cgctctcgac cgtgccggcg ctcggcctca tccagctcat    1980
cgtcttcctc ggcatcatcg aggtgcgctc ggcgaactac cagggccgcg tgcccggcga    2040
ccttggcttt gacccgctcg g                                              2061
```

<210> SEQ ID NO 18
<211> LENGTH: 501
<212> TYPE: PRT
<213> ORGANISM: Pavlova lutherii

<400> SEQUENCE: 18

```
Met Ala Ala Pro Thr Ser Pro Tyr Gly Ala Glu Ser Pro Arg Ala Ala
1               5                   10                  15

Tyr Ala Tyr Pro Glu Arg Ala Asn Val Lys Met Ser Glu Ala Leu Arg
            20                  25                  30

Val Leu Asp Glu Gly Val His Pro Leu Val Ile His Ser Ser Gln Ile
        35                  40                  45

Leu Ala Ala Ala Leu Leu Val Thr Ala Ala Val Asn His Phe Pro Lys
    50                  55                  60

Ile Thr Val Ala Asp Leu Ala Glu Ile Trp Arg Ser Leu Gln Ile Asp
65                  70                  75                  80

Val Ala Tyr Ala Phe Ala Leu Thr Ala Val Ala Leu Leu Leu Gly
                85                  90                  95

Tyr Tyr Ala Leu Arg His Pro Arg Pro Val Tyr Leu Val Asp Phe Ala
            100                 105                 110

Thr Trp Gln Leu Arg Asp Asp Lys Asp Gly Ser Leu Ser Ala Thr
        115                 120                 125

Ser Asp Phe Phe Arg Ser Thr Ile Thr Asp Cys Gly Asn Phe Cys Asp
    130                 135                 140

Glu Ser Val Asp Phe Gln Met Lys Leu Phe Glu Arg Asn Gln Ile Ser
145                 150                 155                 160

Glu Arg Cys Tyr Phe Pro Pro Gly Ile Arg Ala Tyr Arg Lys Gly Glu
                165                 170                 175

Arg Asp Phe Asp Phe Ser Met Ala Ala Ala Arg Lys Glu Phe Glu Thr
            180                 185                 190

Val Val Phe Thr Thr Val Asp Glu Leu Leu Ala Lys Thr Gly Val Lys
        195                 200                 205

Pro Arg Asp Ile Asp Ile Leu Val Val Asn Cys Ser Leu Phe Asn Pro
    210                 215                 220

Thr Pro Ser Leu Ala Ala Ile Val Ile Asn His Tyr Gln Met Lys Asp
225                 230                 235                 240

Ser Val Gln Ser Tyr Ser Leu Gly Gly Met Gly Cys Ser Ala Gly Leu
                245                 250                 255

Ile Ser Ile His Leu Ala Lys Asp Leu Leu Gln Val Tyr Pro Arg Lys
            260                 265                 270
```

```
Arg Ala Leu Val Ile Ser Thr Glu Asn Ile Thr Gln Asn Phe Tyr Gln
        275                 280                 285

Gly Asn Glu Lys Ser Met Leu Ile Ser Asn Thr Leu Phe Arg Met Gly
        290                 295                 300

Gly Ala Ala Val Leu Leu Ser Gly Arg His Ala Asp Arg Arg Val Ala
305                 310                 315                 320

Lys Tyr Gln Leu Leu His Thr Val Arg Thr His Lys Gly Ala Asp Pro
                325                 330                 335

Asp Ala Tyr Arg Cys Val Phe Gln Glu Glu Asp Lys Ala Gly His Val
                340                 345                 350

Gly Val Arg Leu Ser Lys Asp Val Met Glu Cys Ala Gly Ala Ala Met
            355                 360                 365

Lys Thr Asn Ile Ser Val Leu Ala Pro Leu Ile Leu Pro Val Ser Glu
        370                 375                 380

Gln Val Arg Phe Leu Ala Asn Tyr Val Ala Arg Lys Trp Leu Arg Met
385                 390                 395                 400

Lys Gly Val Lys Gly Tyr Val Pro Asp Phe Thr Thr Ala Val Gln His
                405                 410                 415

Phe Cys Ile His Thr Gly Gly Arg Ala Val Leu Asp Ala Leu Gln Ala
                420                 425                 430

Asn Leu Ser Leu Ser Asp Tyr Tyr Leu Glu Pro Ser Arg Tyr Ser Leu
            435                 440                 445

Trp Arg Trp Gly Asn Val Ser Ser Ala Ser Val Trp Tyr Glu Leu Asp
450                 455                 460

Trp Leu Glu Lys Ser Gly Arg Ile Arg Arg Gly Asp Lys Val Trp Gln
465                 470                 475                 480

Ile Gly Phe Gly Ser Gly Phe Lys Cys Asn Ser Ala Val Trp Arg Ala
                485                 490                 495

Cys Arg Ala Met Pro
            500

<210> SEQ ID NO 19
<211> LENGTH: 198
<212> TYPE: PRT
<213> ORGANISM: Pavlova lutherii

<400> SEQUENCE: 19

Ala Arg Gly Leu Asp Leu Leu Pro Ala Leu Arg Gly Lys Met Arg Trp
1               5                   10                  15

Leu Ala Ala Ser Val Leu Phe Arg Leu Pro Ile Val Arg Glu Leu Thr
            20                  25                  30

Leu Trp Thr Gly Cys Ile Asp Ala Arg Arg Ser Val Ala Glu Ser Ala
        35                  40                  45

Leu Arg Gly Gly Tyr Ser Val Gly Val Leu Pro Gly Gly Glu Gln Glu
    50                  55                  60

Gln Leu Arg Thr Arg Tyr Gly Arg Glu Ser Val Tyr Leu Arg Lys Arg
65                  70                  75                  80

Phe Gly Phe Val Lys Leu Ala Leu Arg Phe Gly Val Pro Leu Val Pro
                85                  90                  95

Gly Tyr Val Phe Gly Cys Val Asp Leu Tyr His Thr Ser Ser Leu Leu
                100                 105                 110

Phe Ser Ala Arg Glu Trp Leu Val Arg Ser Leu Gly Val Cys Val Pro
            115                 120                 125

Val Cys Phe Gly Ala Trp Gly Val Pro Met Ala Pro Leu Ala Val Pro
```

```
          130                 135                 140
Leu Asn Val Val Ile Gly Arg Pro Ile Lys Leu Pro Arg Asn Pro Glu
145                     150                 155                 160

Pro Thr Asp Glu Asp Val Ala Arg Ala Leu Asp Gln Tyr Ile Ala Ala
                165                 170                 175

Leu Arg Ala Leu Phe Asp Glu Asn Lys Ala Arg Phe Gly Tyr Ala Asp
                180                 185                 190

Arg Glu Leu Glu Val Cys
            195
```